(12) United States Patent
Uesaka et al.

(10) Patent No.: US 11,957,360 B2
(45) Date of Patent: Apr. 16, 2024

(54) LIGATION DEVICE, APPLICATOR, AND CONNECTION METHOD

(71) Applicant: OLYMPUS CORPORATION, Hachioji (JP)

(72) Inventors: Kensuke Uesaka, Hino (JP); Shinya Ansai, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 512 days.

(21) Appl. No.: 17/357,420

(22) Filed: Jun. 24, 2021

(65) Prior Publication Data

US 2021/0315584 A1 Oct. 14, 2021

Related U.S. Application Data

(63) Continuation of application No. PCT/JP2018/047463, filed on Dec. 25, 2018.

(51) Int. Cl.
*A61B 17/128* (2006.01)
(52) U.S. Cl.
CPC ................ *A61B 17/1285* (2013.01)
(58) Field of Classification Search
CPC .............. A61B 17/1227; A61B 17/128; A61B 17/1285
See application file for complete search history.

(56) References Cited

U.S. PATENT DOCUMENTS

| 6,210,398 B1 | 4/2001 | Ouchi | |
| 9,277,959 B2 * | 3/2016 | Okada | A61B 18/1492 |
| 9,687,248 B2 * | 6/2017 | Satake | A61B 17/122 |
| 2015/0374381 A1 * | 12/2015 | Satake | A61B 17/122 |
| | | | 606/142 |

(Continued)

FOREIGN PATENT DOCUMENTS

| JP | H08-280701 A | 10/1996 |
| JP | H11-332870 A | 12/1999 |

(Continued)

OTHER PUBLICATIONS

Feb. 26, 2019 International Search Report issued in International Patent Application No. PCT/JP2018/047463.

(Continued)

*Primary Examiner* — Ryan J. Severson
(74) *Attorney, Agent, or Firm* — Oliff PLC

(57) ABSTRACT

The ligation device includes a clip unit, an applicator, and the applicator includes a sheath, an operation wire, a second link that is provided on the operation wire, and is capable of being fitted to the first link at a protrusion position, the second link configured to be restricted a releasing of fitting to the first link at an accommodation position, a slider connected to the operation wire and is configured to move with a first operation, and a limiter including a switch member configured to move in an intersecting direction that intersects a direction of the first operation with a second operation. The limiter is configured to limit a movement range of the slider when the second operation is not performed, and configured to release a limitation of the movement range of the slider with the second operation and to allow the second link to move toward the protrusion position.

14 Claims, 18 Drawing Sheets

(56) References Cited

U.S. PATENT DOCUMENTS

| | | | |
|---|---|---|---|
| 2021/0315584 A1* | 10/2021 | Uesaka | A61B 17/1285 |
| 2021/0315585 A1* | 10/2021 | Tsuji | A61B 17/122 |
| 2022/0175387 A1* | 6/2022 | Tsuji | A61B 17/1227 |

FOREIGN PATENT DOCUMENTS

| | | |
|---|---|---|
| JP | 2005-218683 A | 8/2005 |
| JP | 2006-187673 A | 7/2006 |
| JP | 2008-289524 A | 12/2008 |
| JP | 2009-261609 A | 11/2009 |
| JP | 2012-200518 A | 10/2012 |
| JP | 2013-085859 A | 5/2013 |

OTHER PUBLICATIONS

Oct. 18, 2022 Office Action issued in Japanese Application No. 2020-561984.

\* cited by examiner

FIG. 1
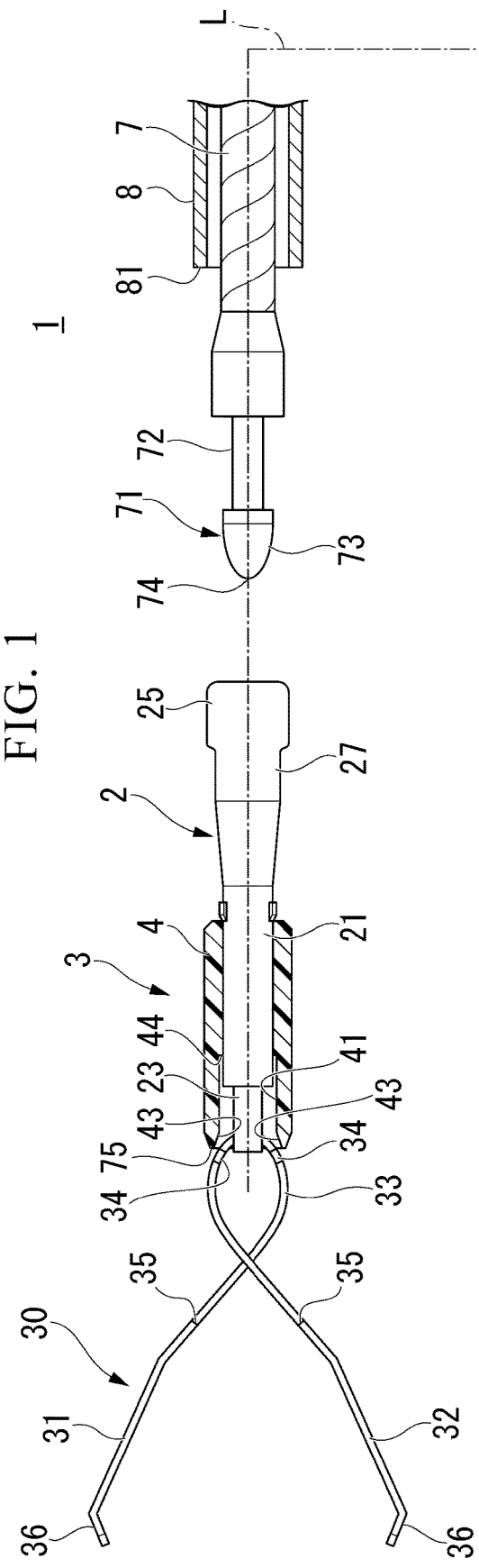
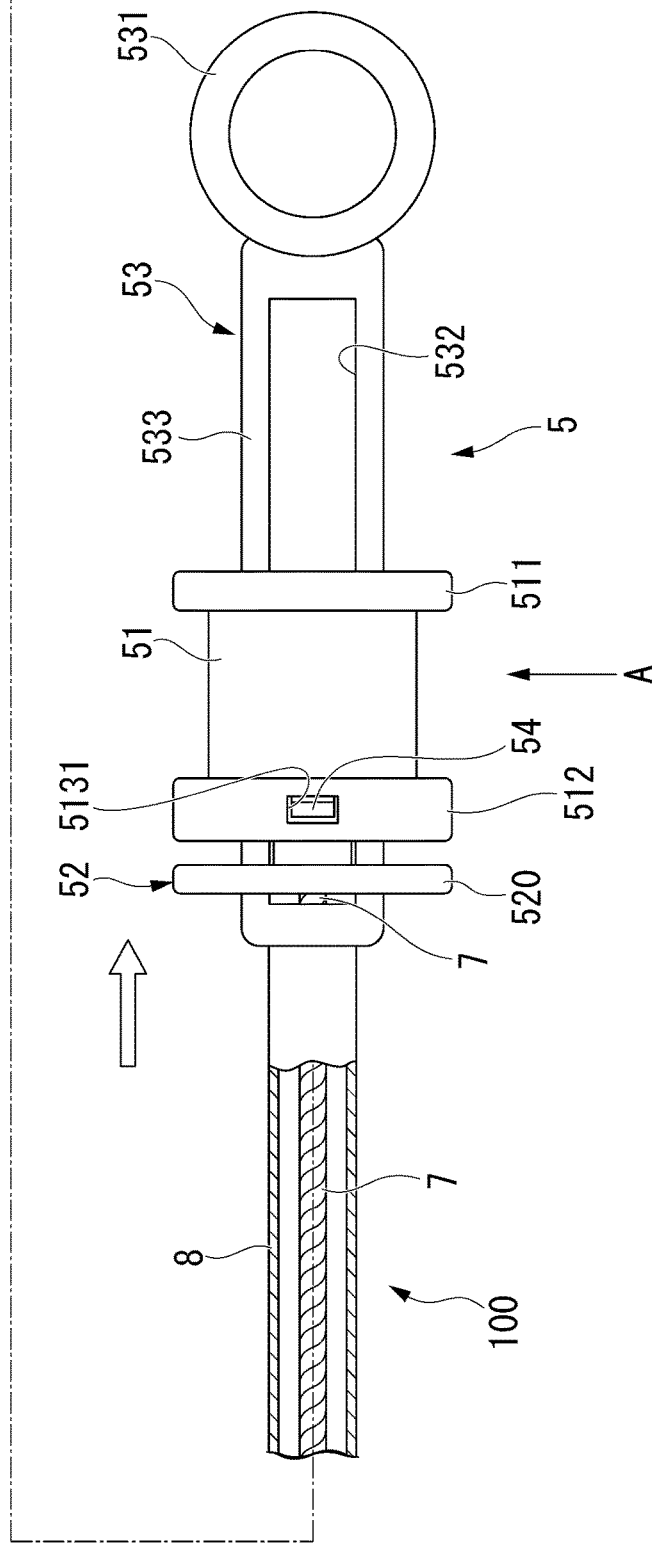

LIGATION DEVICE, APPLICATOR, AND CONNECTION METHOD

The present invention relates to a ligation device, an applicator, and a connection method. This application is a continuation application based on International Patent Application No. PCT/JP 2018/047463 filed on Dec. 25, 2018, and the content of the PCT international application is incorporated herein by reference.

BACKGROUND ART

A clip device for an endo scope (a treatment tool for an endoscope) that ligates treatment target tissue with a clip to close an opening formed in living tissue, to stop bleeding, or the like is known (for example, Japanese Unexamined Patent Application, First Publication No. 2012-200518). In the clip device for an endoscope, a sheath is inserted into a channel of an endoscope and is inserted into the body via the channel.

In the treatment tool for an endoscope of Japanese Unexamined Patent Application, First Publication No. 2012-200518, a connection hook connected to the distal end of a drive wire is advanced and retracted with respect to the sheath by an operation of sliding a slider unit to which the drive wire is connected with respect to a base portion. Depending on the position of the connection hook with respect to the sheath, the position of the connection hook is changed to a clip opening position where the clip is opened, a clip connecting position where the clip is connected, and a clip fastening position where the clip is fastened to the connection hook. A plurality of positioning grooves is formed in the base portion, and when the slider unit is fitted to any one of the positioning grooves, the connection hook is positioned at the clip opening position, the clip connecting position, or the clip fastening position.

The treatment tool for an endoscope of Japanese Unexamined Patent Application, First Publication No. 2012-200518 has a configuration in which the pressing of the connection hook by the sheath is released and the clip is opened when the slider unit is positioned at the clip opening position.

On the other hand, when the clip is opened and closed at the clip connecting position, the clip is advanced and retracted with respect to a clip closing ring by an operation of an operation wire. Therefore, it is preferable that the clip and the clip closing ring be stably held at the distal end of the sheath.

In addition, there is a clip device for an endoscope having a reload function. The reload function is a function of mounting (reloading) the next clip on an applicator, after first ligating the tissue with a clip, for example, in a case where a plurality of portions of the treatment target tissue are ligated with clips.

In addition, there is a clip device for an endoscope having a re-gripping operation function of the tissue with a clip. By providing the re-gripping operation function, for example, in a case where the unintended tissue is erroneously gripped by a clip, it is possible to grip the tissue again after the gripping state of the tissue by the clip is released once.

SUMMARY

According to a first aspect is a ligation device including a clip unit having a first link; and an applicator. The applicator includes: a sheath; an operation wire inserted into the sheath and configured to operate the clip unit, a second link provided on the operation wire and is capable of being fitted to the first link at a protrusion position where the second link protrudes from the sheath; the second link being configured to be restricted a releasing of fitting to the first link at an accommodation position where the second link is accommodated in the sheath; a slider connected to the operation wire and is configured to move with a first operation; and a limiter including a switch member configured to move in an intersecting direction that intersects a direction of the first operation with a second operation. The limiter is configured to limit a movement range of the slider when the second operation is not performed, and configured to release a limitation of the movement range of the slider with the second operation and to allow the second link to move toward the protrusion position.

According to a second aspect, in the ligation device of the first aspect, when the first link and the second link are fitted to each other and the slider is advanced maximally in a state where the movement range of the slider is limited by the limiter, a connection portion between the first link and the second link may be located in the sheath.

According to a third aspect, in the ligation device of the first aspect, the clip unit may have a c holding tube having a cylindrical shape and into which at least one of the first arm and the second arm is able to be inserted, and the first link may be disposed to protrude from the holding tube to a proximal side.

According to a fourth aspect, in the ligation device of the third aspect, when the first link and the second link are fitted to each other and the slider is advanced maximally in a state where the movement range of the slider is limited by the limiter, the holding tube and the sheath may come into contact with each other.

According to a fifth aspect, in the ligation device of the first aspect, the slider may move be configured to move the second link by advancing and retracting.

According to a sixth aspect, in the ligation device of the fifth aspect, the applicator may include a handle to which the slider is attached to be able to advance and retract. The limiter may include: a first contact surface that is able to come into contact with the handle; and a second contact surface that is able to come into contact with the slider. At least one of the first contact surface and the second contact surface may be provided on the switch member and may be configured to be movable together with the switch member in the intersecting direction.

According to a seventh aspect, in the ligation device of the first aspect, the slider may be configured to move the second link by advancing and retracting. The switch member may be rotatable around an advance and retract direction of the slider. The limiter may be configured to release the limitation of the movement range of the slider by the switch member being rotated with the second operation.

According to an eighth aspect, in the ligation device of the seventh aspect, the applicator may include a handle to which the slider is attached to be able to advance and retract. The limiter may include a first contact surface which is able to come into contact with the handle, and a second contact surface which is able to come into contact with the slider, and at least one of the first contact surface and the second contact surface may be provided on the switch member and may be able to move in a rotation direction of the switch member along with the rotation of the switch member.

According to a ninth aspect is an applicator including a sheath; an operation wire inserted into the sheath and configured to be capable of being connected with a clip unit; a link connected to the operation wire and configured to be capable of being fitted to the clip unit at a protrusion position where the link protrudes from the sheath, the link being configured to be restricted a releasing of fitting to the clip unit at an accommodation position where the link is accommodated in the sheath; a slider connected to the operation wire and is configured to move with a first operation; and a limiter including a switch member configured to move in an intersecting direction that intersects a direction of the first operation with a second operation. The limiter is configured to limit a movement range of the slider and maintain the link in the accommodation position when the second operation is not performed, and configured to release a limitation of the movement range of the slider with the second operation and to allow the link to move toward the protrusion position.

According to a tenth aspect, in the applicator of the ninth aspect, the slider may be configured to move the link by advancing and retracting.

According to an eleventh aspect, in the applicator of the tenth aspect, the applicator may include a handle to which the slider is attached to be able to advance and retract. The limiter may include: a first contact surface which is able to come into contact with the handle, and a second contact surface which is able to come into contact with the slider. At least one of the first contact surface and the second contact surface may be provided on the switch member and may be able to move together with the switch member in the intersecting direction.

According to a twelfth aspect, in the applicator of the ninth aspect, the slider may be configured to move the operation wire by advancing and retracting. The switch member may be rotatable around an advance and retract direction of the slider. The limiter may be configured to release the limitation of the movement range of the slider by the switch member being rotated with the second operation.

According to a thirteenth aspect, in the applicator of the ninth aspect, the slider may be configured to move the link by advancing and retracting. The switch member may be rotatable around an advance and retract direction of the slider. The limiter may be configured to release the limitation of the movement range of the slider by the switch member being rotated with the second operation.

According to a fourteenth aspect is a connection method of a clip unit in a ligation device including: a clip unit that has a first link; a second link provided at a distal end of an operation wire inserted into a sheath; a slider connected to the operation wire; and a limiter configured to limit a movement range of the slider. The method includes a release step which is executed in a state where the movement range of the slider is restricted by the limiter and releasing a limitation of the movement range of the slider by the limiter with a second operation to operate in an intersecting direction that intersects a moving direction of the slider that is moved with a first operation; a first moving step of moving the second link with the first operation from an accommodation position where the second link is accommodated in the sheath to a protrusion position where the second link protrudes from the sheath; a fitting step of fitting the second link to the first link at the protrusion position; a second moving step of moving the second link that is fitted to the first link with the first operation to the accommodation position; and a limiting step of limiting the movement range of the slider by the limiter again with the second operation.

BRIEF DESCRIPTION OF THE DRAWINGS

FIG. 1 is a partial cross-sectional view showing a ligation device according to a first embodiment.

DESCRIPTION OF EMBODIMENTS

First Embodiment

Figure 2:
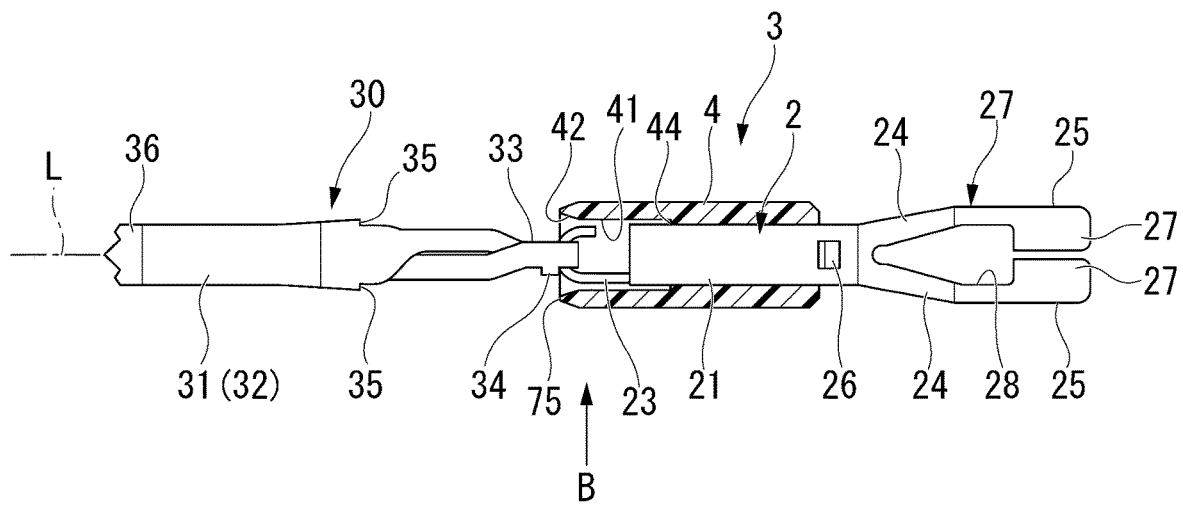
FIG. 2 is a partial cross-sectional view showing a clip unit of the first embodiment.
Figure 3:
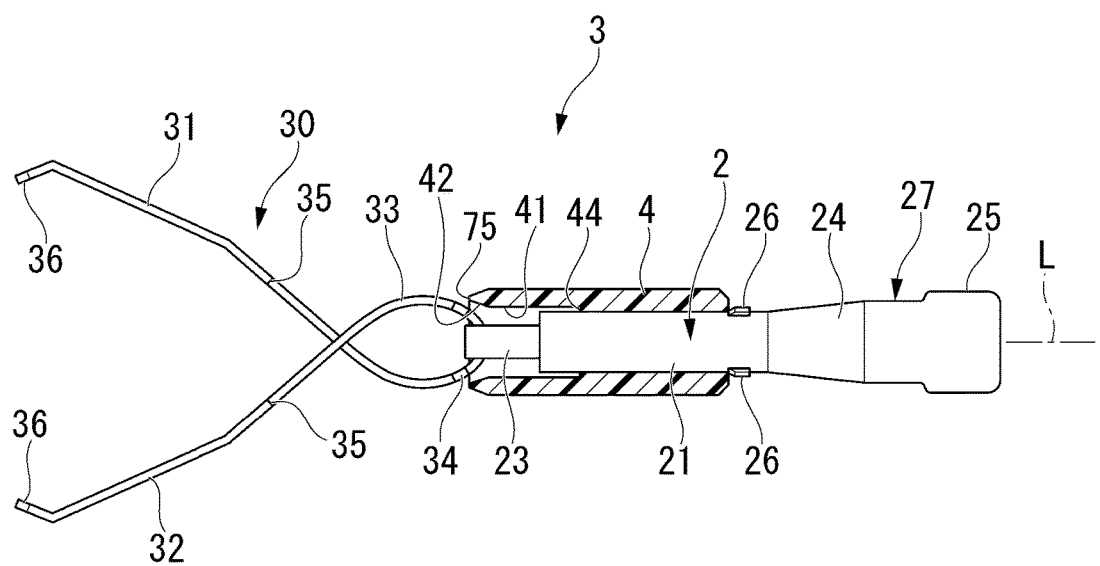
FIG. 3 is a partial cross-sectional view showing the clip unit of the first embodiment.
Figure 4:
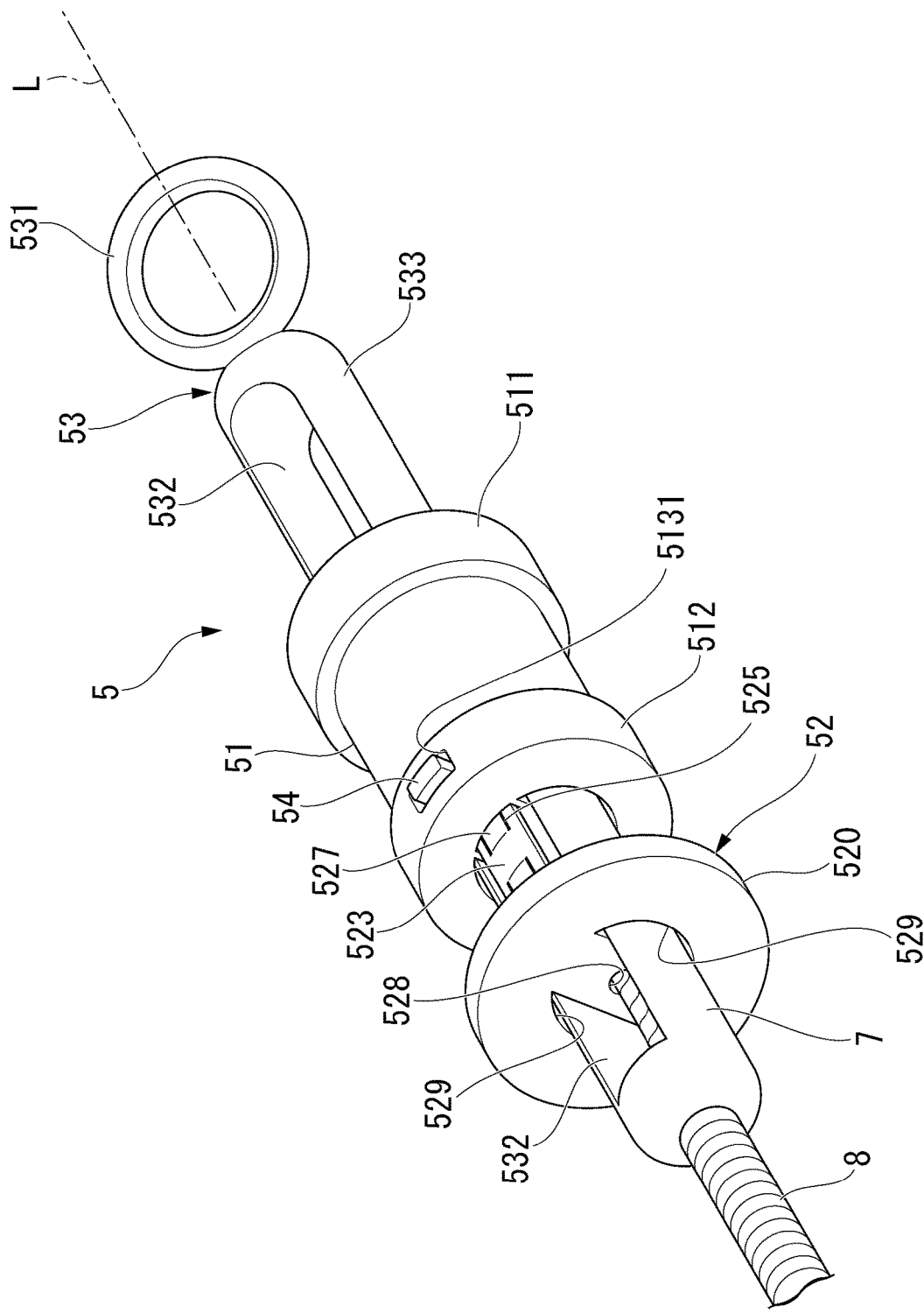
FIG. 4 is a perspective view showing a handle of the ligation device according to the first embodiment.
Figure 5:
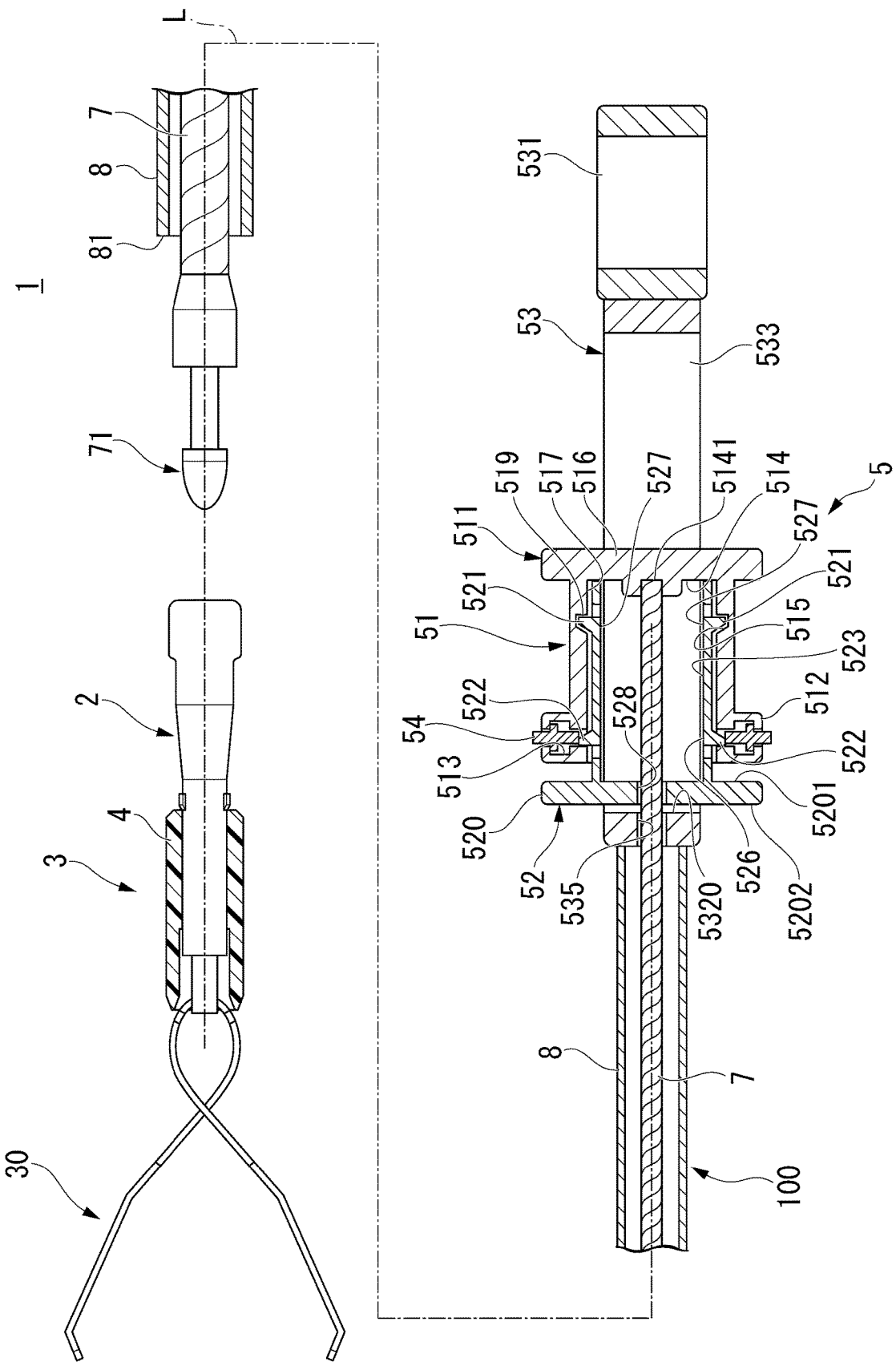
FIG. 5 is a cross-sectional view of the ligation device according to the first embodiment in a longitudinal axis direction, in which the handle is seen in a direction of arrow A shown in FIG. 1.
Figure 6:
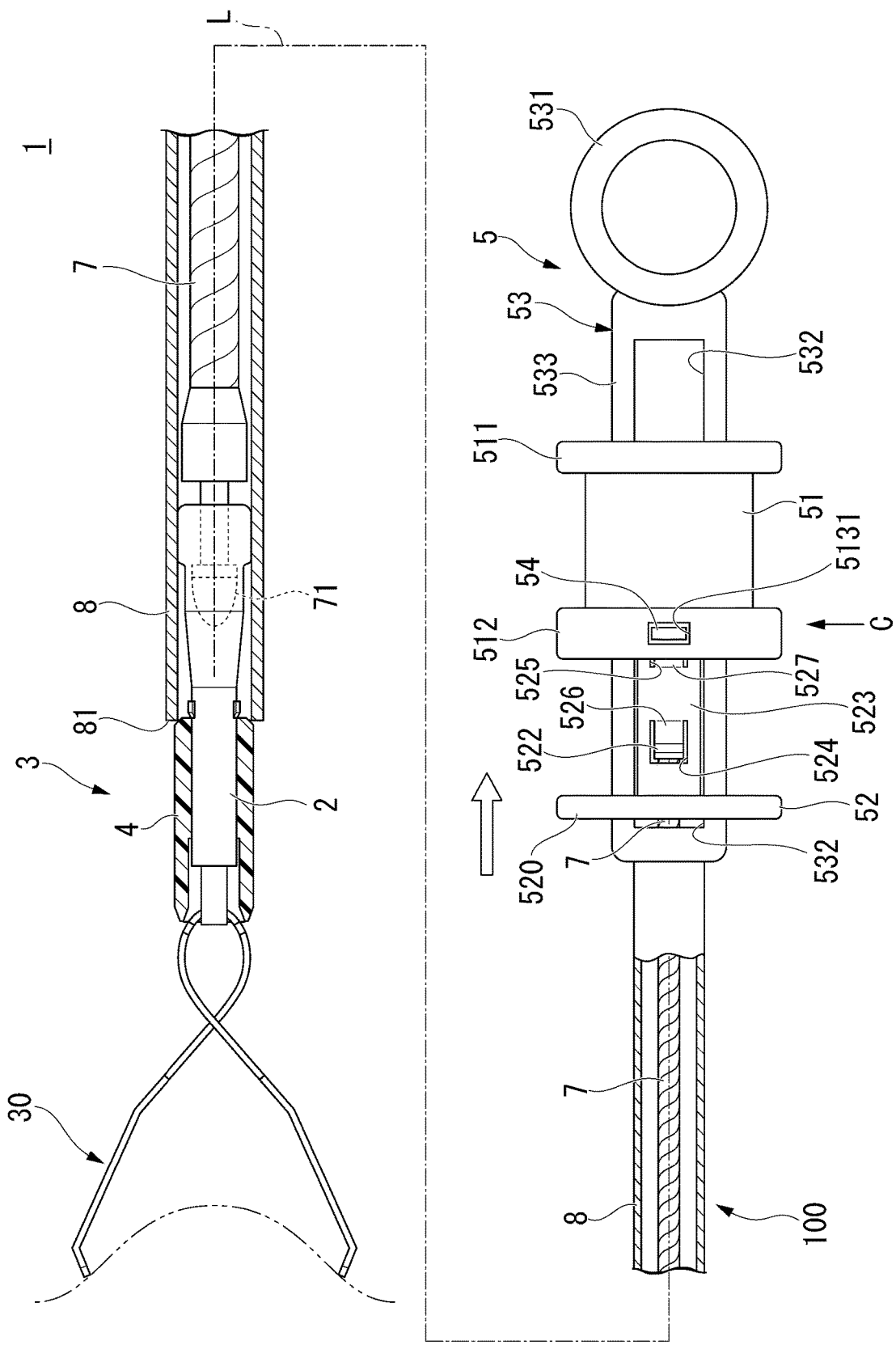
FIG. 6 is a partial cross-sectional view showing the ligation device according to the first embodiment.
Figure 7:
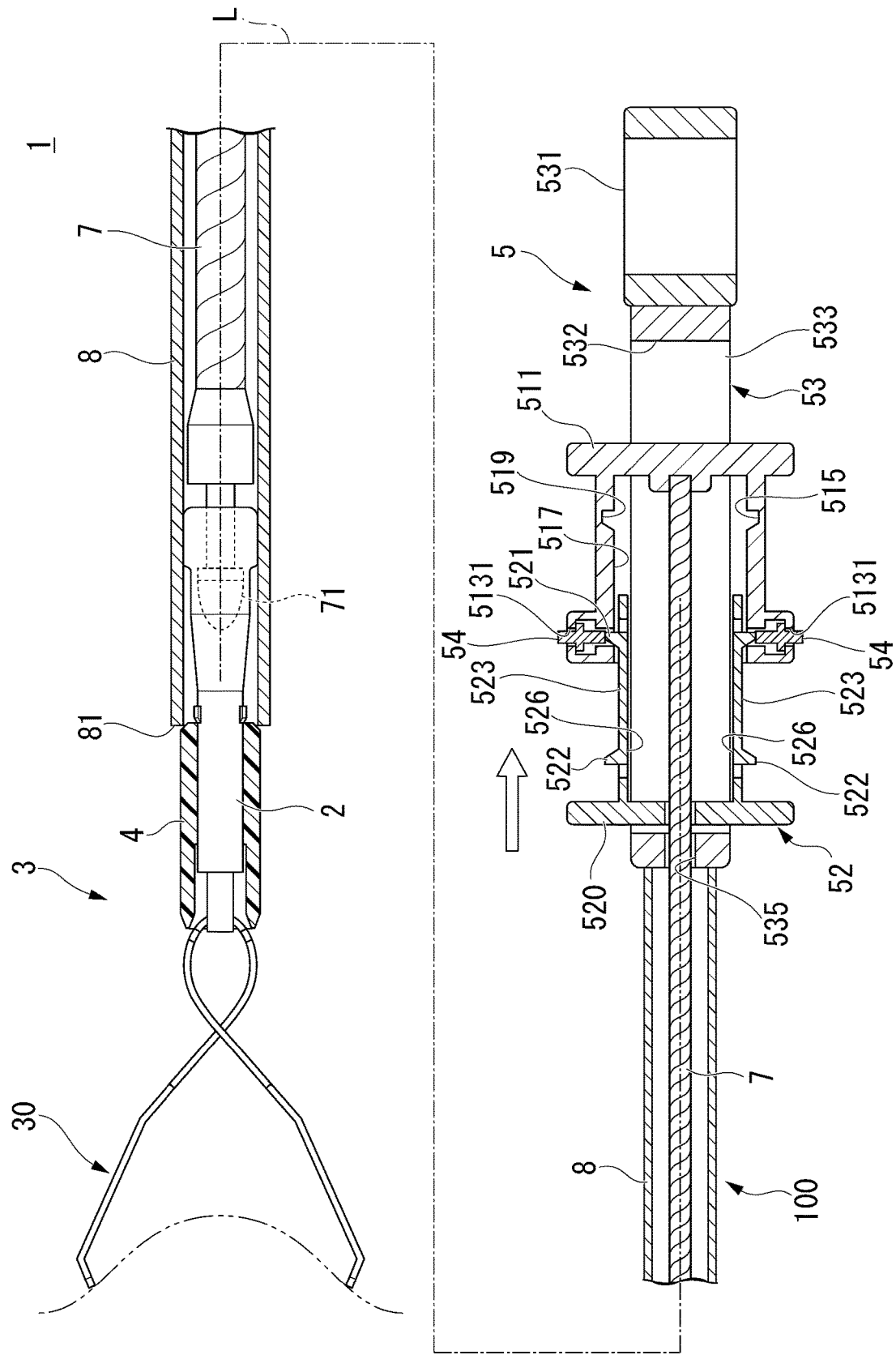
FIG. 7 is a cross-sectional view of the ligation device according to the first embodiment in the longitudinal axis direction, in which the handle is seen in a direction of arrow C shown in FIG. 6.
Figure 8:
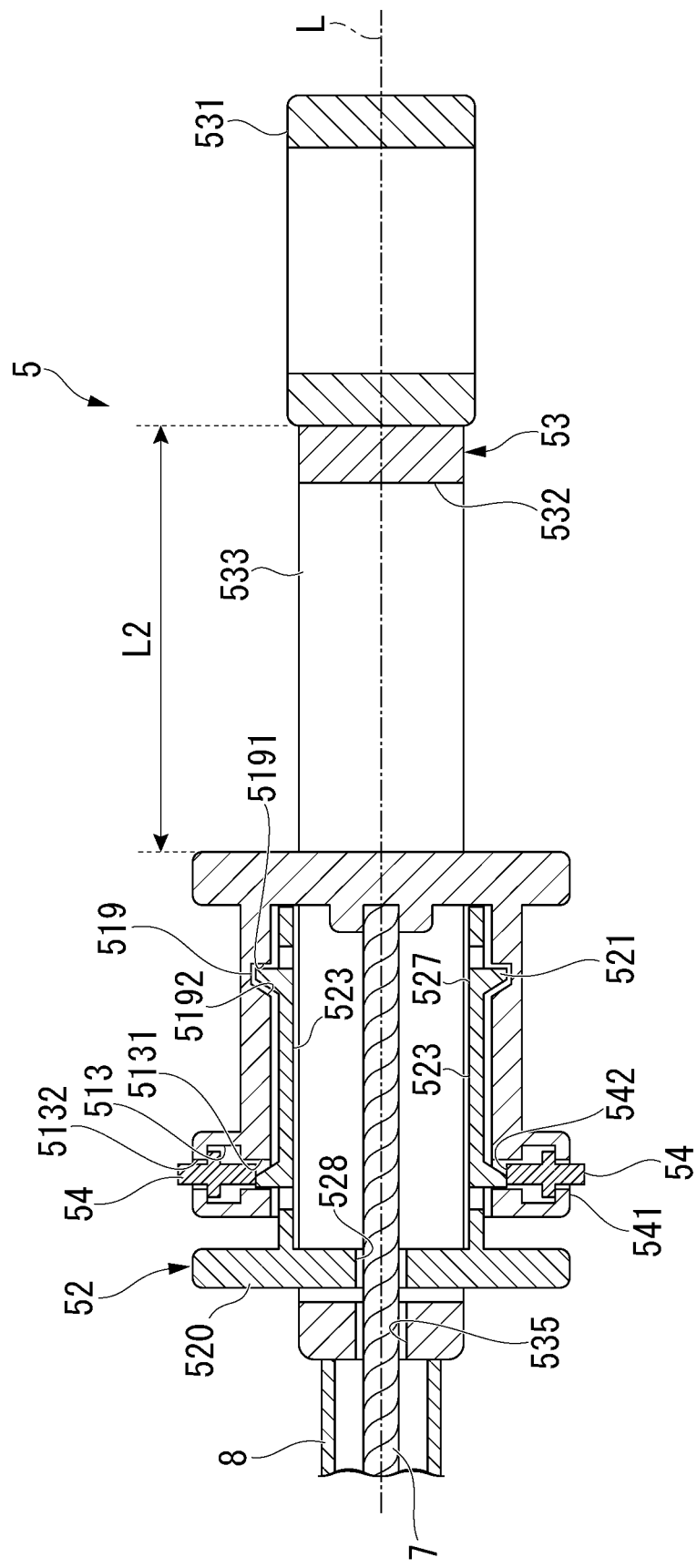
FIG. 8 is an enlarged cross-sectional view of an operation unit of FIG. 5.
Figure 9:
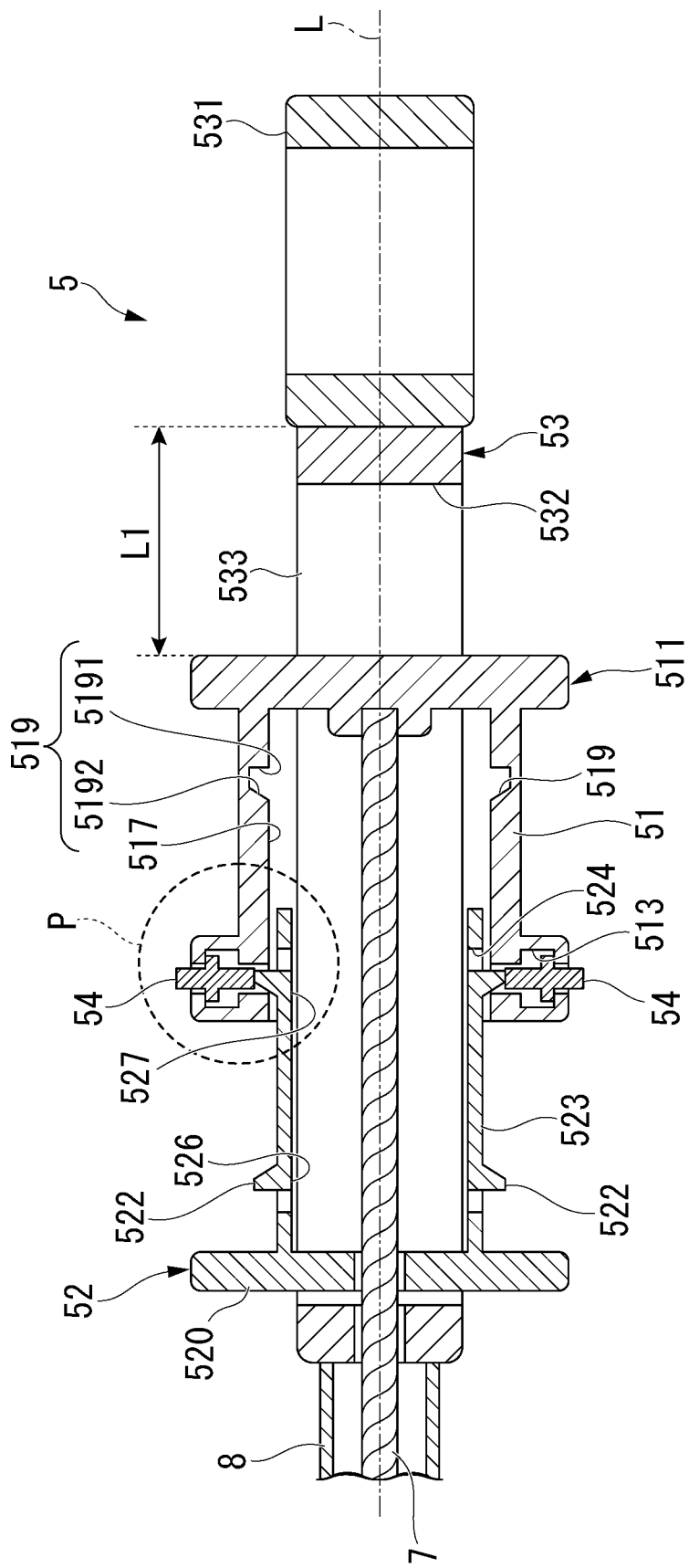
FIG. 9 is an enlarged cross-sectional view of the operation unit of FIG. 7.

A ligation device and a connection method according to a first embodiment will be described with reference to FIGS. 1 to 9. FIG. 1 is an overall view showing a ligation device 1 according to the present embodiment. FIGS. 2 and 3 are partial cross-sectional views showing a clip unit 3 of the present embodiment. FIG. 4 is a perspective view showing an operation unit 5 of the ligation device 1. FIGS. 5 and 7 are cross-sectional views of the ligation device 1 in a longitudinal axis direction. The operation unit 5 in FIG. 5 is seen in a direction of arrow A shown in FIG. 1. FIG. 6 is a partial cross-sectional view showing the ligation device 1 according to the present embodiment. The operation unit 5 in FIG. 7 is seen in a direction of arrow C shown in FIG. 6. FIGS. 8 and 9 are cross-sectional views of the operation unit 5.

The ligation device 1 according to the present embodiment is a device which is inserted into a body via a treatment tool channel of an endoscope and ligates body tissue with the clip unit 3. As shown in FIG. 1, the ligation device 1 includes the clip unit 3 and an applicator 100. The applicator 100 includes a sheath 8, an operation wire 7, a connector 71 (a second link), and the operation unit 5.

In the following description, the center line in a longitudinal direction in a state where the ligation device 1 extends in a straight line is referred to as a longitudinal axis L. The operation unit 5 side in the ligation device 1 is referred to as a proximal side, and a side which is opposite to the proximal side in a longitudinal axis L direction and on which the clip unit 3 is provided is referred to as a distal side.

In the ligation device 1, the proximal end of the sheath 8 is connected to the distal portion of the operation unit 5, and the operation wire 7 is inserted from the operation unit 5 over the entire length of the sheath 8. The operation wire 7 is provided to be able to advance and retract with respect to the sheath 8. The clip unit 3 is detachably connected to the connector 71 at the distal end of the operation wire 7, and an arm member 30 is placed at a treatment target portion with an operation of the operation unit 5. A specific configuration of each part of the ligation device 1 will be described below.

The clip unit 3 will be described. FIGS. 2 and 3 are partial cross-sectional views in the longitudinal axis L direction of the clip unit 3, which schematically show the clip unit 3 of the present embodiment. FIG. 3 is a view seen in a direction of arrow B shown in FIG. 2. As shown in FIGS. 2 and 3, the clip unit 3 includes the arm member 30, a holding tube 4, and a connecting rod 2 (a first link).

The arm member 30 has a first arm 31, a second arm 32, and a connecting portion 33.

The arm member 30 is manufactured with, for example, a thin and elongated plate made of a metal such as stainless steel, a cobalt-chromium alloy, and titanium. In the arm member 30, the connecting portion 33 is formed by the thin and elongated plate being bent in a thickness direction in the intermediate portion thereof, and both ends of the plate become the first arm 31 and the second arm 32. In the arm member 30, the connecting portion 33 is disposed on the proximal side of the first arm 31 and the second arm 32. The first arm 31 and the second arm 32 intersect at the distal side of the connecting portion 33, and the first arm 31 and the second arm 32 extend away from each other in a distal side direction.

A pair of projecting pieces 34 is formed in the connecting portion 33. The pair of projecting pieces 34 projects outward in a direction orthogonal to the longitudinal direction in which the first arm 31 and the second arm 32 extend. The pair of projecting pieces 34 may be formed at positions which are line-symmetrical with respect to the central axis in the longitudinal direction.

Claw portions 36 bent toward each other are formed at ends of the first arm 31 and the second arm 32 opposite to the connecting portion 33. The first arm 31 and the second arm 32 are each provided with a tendency to bend away from each other from the connecting portion 33 side toward the claw portion 36 side.

The holding tube 4 is a cylindrical member having an insertion hole 41 penetrating the holding tube 4 in the longitudinal axis L direction. The insertion hole 41 is a circular hole and is formed to penetrate the holding tube 4 from the distal end to the proximal end thereof. The insertion hole 41 has an inner diameter into which at least a part of the arm member 30 is allowed to be inserted. A tapered surface 42 is formed on the inner wall of the distal end portion of the insertion hole 41. The tapered surface 42 is formed to expand in diameter toward a distal end surface 75 of the holding tube 4. In the intermediate region of the insertion hole 41, a step portion 44 having an inner diameter smaller than that on the distal side thereof is formed. The outer diameter of the holding tube 4 is larger than the inner diameter of the sheath 8 of the applicator 100, which will be described later.

The holding tube 4 is manufactured using, for example, a metal material such as stainless steel, a titanium alloy (Ti-6AL-4V or the like), or a cobalt-chromium alloy, or a high rigidity resin material having appropriate elasticity such as polyphthalamide (PPA), polyamide (PA), or the like.

The connecting rod 2 is a member that connects the arm member 30 and the operation wire 7 to each other, which will be described later. As shown in FIGS. 2 and 3, the connecting rod 2 has a connecting main body 21, a hook portion 23, a proximal fitting portion 27, and a locking projection 26. The connecting rod 2 is formed of a resin material or the like having a predetermined strength.

It is sufficient for the connecting main body 21 to have a size that allows it to be inserted into the insertion hole 41 of the holding tube 4, and the shape thereof is not limited. The connecting main body 21 of the present embodiment has a substantially circle columnar shape, and the outer diameter of the connecting main body 21 is smaller than the inner diameter of the insertion hole 41 of the holding tube 4. The hook portion 23 is provided at the distal end of the connecting main body 21, and the proximal fitting portion 27 is provided at the proximal end thereof.

The hook portion 23 is provided to project from the distal end of the connecting main body 21 in the distal side direction. The hook portion 23 has a shape bent in a direction intersecting the central axis of the connecting main body 21 having a circle columnar shape. The hook portion 23 is configured such that the connecting portion 33 of the arm member 30 is capable of being locked thereto. The hook portion 23 is located inside the outer circumference of the connecting main body 21 when the connecting rod 2 is seen from the distal side and has a dimension that allows it to be inserted into the insertion hole 41 of the holding tube 4.

The proximal fitting portion 27 is configured to be able to be fitted to the connector 71 of the operation wire 7. The proximal fitting portion 27 is connected to the proximal end of the connecting main body 21 and extends in a proximal side direction. As shown in FIG. 2, the proximal fitting portion 27 has a fitting hole 28, a pair of legs 24, and a proximal locking end 25. In the proximal fitting portion 27, the pair of legs 24 extends toward the proximal side from the connecting main body 21, and the fitting hole 28 is formed between the distal portions of the pair of legs 24. The fitting hole 28 has a size that allows the connector 71 of the operation wire 7 to be inserted into the fitting hole 28, which will be described later.

The proximal locking end 25 is formed to project toward the central axis of the connecting rod 2 such that the separation distance between the proximal ends of the pair of legs 24 is narrowed. The proximal locking end 25 is configured to narrow an opening of the fitting hole 28 on the proximal side. When an external force is applied, the leg 24 elastically deforms outward in a radial direction of the connecting rod 2, and a pair of proximal locking ends 25 is separated from each other and expands to a dimension that allows the connector 71 to enter the fitting hole 28.

The locking projection 26 is provided on the outer circumferential surface of the proximal portion of the connecting main body 21 to project in the radial direction. As shown in FIG. 3, two locking projections 26 are provided at symmetrical positions with the central axis of the connecting main body 21 interposed therebetween. The two locking projections 26 project to the extent that the locking projections 26 cannot enter the insertion hole 41 of the holding tube 4. The locking projection 26 restricts an advance movement position of the connecting rod 2 with respect to the holding tube 4. In a case where the connecting rod 2 is inserted into the insertion hole of the holding tube 4 and is advanced, the locking projection 26 comes into contact with the proximal end of the holding tube 4 to restrict further advance movement of the connecting rod 2.

In the connecting rod 2, the hook portion 23 and the connecting main body 21 are inserted into the insertion hole 41 of the holding tube 4. The connecting rod 2 is capable of advancing and retracting with respect to the holding tube 4 to a position where the locking projection 26 comes into contact with the proximal end of the holding tube 4. When the locking projection 26 comes into contact with the proximal end of the holding tube 4, the advance movement of the connecting rod 2 with respect to the holding tube is restricted. A loop portion of the connecting portion 33 of the arm member 30 is locked to the hook portion 23. Therefore, the connecting rod 2 and the arm member 30 are inserted into the holding tube 4 to be able to advance and retract.

Although not shown, the clip unit 3 is accommodated in a clip cartridge before being connected to the connector 71 for the purpose of ease of transportation, ease of a mounting operation at the time of reloading, maintenance of a sterilized state, and the like.

Next, the configuration of the applicator 100 will be described. As shown in FIG. 1, the applicator 100 includes the operation unit 5, the sheath 8, and the operation wire 7. The applicator 100 is provided with the operation unit 5 at the proximal end of the sheath 8, and the operation wire 7 connected to the operation unit 5 is inserted into the sheath 8. The applicator 100 is configured such that the operation wire 7 is movable relative to the sheath 8 in the longitudinal direction with the operation of the operation unit 5.

The sheath 8 is a flexible and long tubular member. The sheath 8 has a conduit formed along the longitudinal axis L over its entire length. The sheath 8 is, for example, a coil sheath formed by winding a wire made of stainless steel such as SUS 301 tightly around the longitudinal axis L. The proximal end of the sheath 8 is connected to a handle 53 of the operation unit 5. The conduit is open to a distal end 81 of the sheath 8.

The operation wire 7 is inserted into the sheath 8. The proximal end of the operation wire 7 is fixed to a first slider 51 of the operation unit 5, which will be described later, and the connector 71 is fixed to the distal end of the operation wire 7. The operation wire 7 is made of a single metal wire or a stranded wire.

The connector 71 is a member that is capable of being connected to the clip unit 3. Specifically, the connector 71 is a member that connects the arm member 30 and the operation wire 7 to each other. The connector 71 includes a shaft 72 configured to be located at the proximal portion thereof and a large diameter portion 73 located at the distal portion thereof. The proximal end of the shaft 72 is fixed to the distal end of the operation wire 7. The large diameter portion 73 has a conical shape having a diameter larger than that of the shaft 72, projects in the longitudinal axis L direction, and has a tip end 74 disposed on the distal side thereof.

As shown in FIGS. 1, 4 and 5, the operation unit 5 includes the handle 53, the first slider 51 (a slider), and a second slider 52 (a limiter).

The handle 53 is a rod-shaped member extending in the longitudinal axis L direction and has an elongated hole 532 in the central portion. The elongated hole 532 extends in the longitudinal axis L direction between the distal end portion and the proximal end portion of the handle 53 and penetrates the handle 53 in a direction orthogonal to the longitudinal axis L direction of the handle 53. A finger hooking hole 531 is provided at the proximal end of the handle 53. In the present embodiment, an example in which the finger hooking hole 531 is a through hole is illustrated, but a finger hooking portion does not have to be a through hole. For example, the finger hooking portion may be configured to have a recess to which a finger is hooked to hold the handle 53. The distal end of the handle 53 is fixed to the sheath 8.

A wire insertion hole 535 is formed at the distal end portion of the handle 53. The wire insertion hole 535 is formed to penetrate the handle 53 along the longitudinal axis L between the distal end surface of the handle 53 and the distal end of the elongated hole 532. As shown in FIG. 5, the operation wire 7 is inserted into the wire insertion hole 535 of the handle 53, and the proximal end of the operation wire 7 is fixed to the first slider 51.

The first slider 51 has a substantially cylindrical shape. The first slider 51 is externally attached with respect to the handle 53 to be slidable in the longitudinal axis L direction. As shown in FIGS. 5 and 7, the first slider 51 has an insertion hole 517 extending in the longitudinal axis L direction. The insertion hole 517 has a shape similar to the outer circumferential shape of the handle 53 in the direction orthogonal to the longitudinal axis L and is formed in a size that allows the handle 53 to slide in the insertion hole 517. It is configured that the handle 53 is inserted into the insertion hole 517 and the first slider 51 is slidable with respect to the handle 53.

The proximal end portion of the insertion hole 517 has a proximal end wall extending in a direction orthogonal to the longitudinal axis L direction. The proximal end wall has a proximal opening into which the handle 53 is insertable. The distal end of the first slider 51 opens along the opening shape of the insertion hole 517.

The proximal end portion of the first slider 51 is provided with a proximal wall portion 516 orthogonal to the longitudinal axis L direction. A wire fixing portion 5141 for fixing the operation wire 7 is formed at a substantially central portion of an inner surface 514 of the proximal wall portion 516 which faces the insertion hole 517.

A proximal finger hooking wall portion 511 and a distal finger hooking wall portion 512 that project outward in the radial direction are provided at both end portions of the first slider 51 in the longitudinal direction. As shown in FIGS. 4 and 5, a hollow portion 513 is formed in the distal finger hooking wall portion 512 at the distal end portion of the first slider 51. As shown in FIG. 8, the hollow portion 513 communicates with an inner hole 5131 and an outer hole 5132. The inner hole 5131 is a hole that communicates with the hollow portion 513 and the insertion hole 517 and extends in the radial direction of the first slider 51. The outer hole 5132 is a hole that communicates with the hollow portion 513 and the outer circumferential surface of the first slider 51 and extends in the radial direction of the first slider 51. The inner hole 5131 and the outer hole 5132 are formed on the same straight line in the radial direction of the first slider 51.

Figure 10:
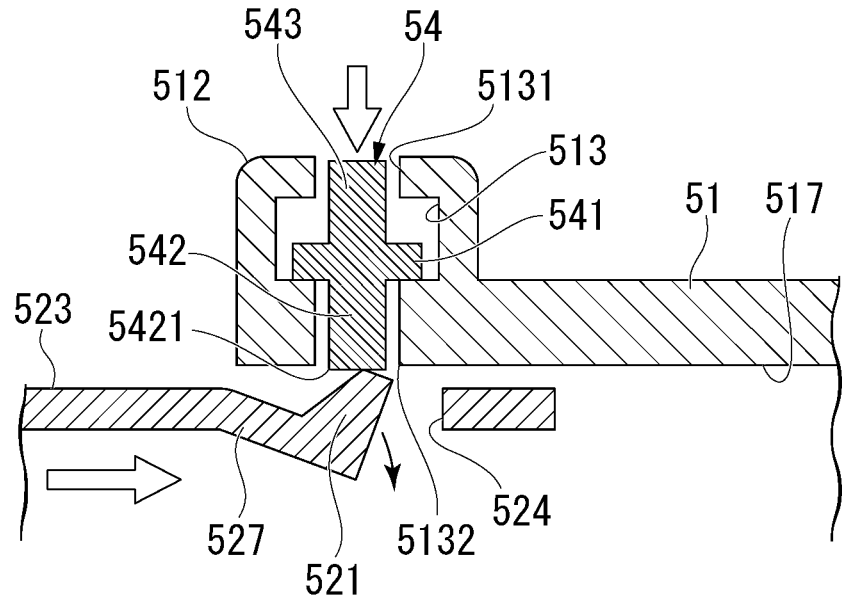
FIG. 10 is a cross-sectional view of a portion indicated by reference sign P in FIG. 9, which shows an aspect of a slider unit.

A switch member 54 is provided in the hollow portion 513. The switch member 54 includes a switch main body 541, an outer projecting portion 543, and an inner projecting portion 542 (see FIG. 10). The switch main body 541 is inserted into the hollow portion 513 and has a dimension that allows it to move in the hollow portion 513 in the radial direction. The outer projecting portion 543 and the inner projecting portion 542 project from the switch main body 541 in opposite directions to each other. The outer projecting portion 543 is disposed to be able to advance and retreat in the outer hole 5132 in the radial direction of the first slider 51. That is, the switch member 54 is configured to be movable in a direction intersecting an advance and retract movement direction of the first slider 51. The inner projecting portion 542 is disposed to be able to advance and retreat in the inner hole 5131 in the radial direction of the first slider 51. The inner side surface of the inner projecting portion 542 is a contact surface 5421 (a second contact surface) which is able to come into contact with the second slider 52. A biasing member (not shown) is provided between the switch member 54 and the hollow portion 513. In a natural state in which an external force is not applied in the radial direction, the switch member 54 is biased outward in the radial direction, and the outer projecting portion 543 projects outward from the outer hole 5132 and is held in that state.

As shown in FIGS. 8 and 9, a locking recess 519 which is recessed outward in the radial direction is formed in the inner wall of the proximal end portion of the insertion hole 517. A proximal end surface 5191 of the locking recess 519 is a plane orthogonal to the longitudinal axis L, and a distal end surface 5192 of the locking recess 519 is an inclined surface which is inclined with respect to the longitudinal axis L such that its diameter decreases toward the distal side.

The hollow portion 513 and the locking recess 519 are each provided at two locations with separated from each other in a circumferential direction of the first slider 51. The hollow portion 513 and the locking recess 519 are formed such that the positions thereof on the first slider 51 in the circumferential direction coincide with each other.

The second slider 52 is provided on the distal side from the first slider 51. The second slider 52 is provided to be slidable along the elongated hole 532 of the handle 53 in the longitudinal axis L direction. As shown in FIGS. 4 and 5, the second slider 52 includes a distal wall portion 520 and a side wall portion 523. The distal wall portion 520 has a substantially disk shape, and a pair of slide holes 529 and a wire insertion hole 528 are formed to penetrate the distal wall portion 520 in the longitudinal axis L direction. The side portions of the elongated holes 532 of the handle 53 are inserted through the pair of slide holes 529. The wire insertion hole 528 is formed in the central portion of the second slider 52.

The side wall portion 523 is a side wall provided to project in the longitudinal axis L direction from a proximal end surface 5201 of the distal wall portion 520. As shown in FIG. 5, the side wall portion 523 is provided with a first projection 521 and a second projection 522. The first projection 521 is provided on the proximal side of the second slider 52, and the second projection 522 is provided on the distal side of the second slider 52. The first projection 521 and the second projection 522 are projections that project outward in the radial direction of the second slider 52, respectively. Slits 524 and 525 penetrating the side wall portion 523 in a thickness direction (the radial direction of the second slider 52) are formed around the first projection 521 and the second projection 522 (see FIGS. 4 and 6). When the second slider 52 is seen from the outside in the radial direction, the slits 524 and 525 are formed in a substantially U shape. The first projection 521 is connected to the side wall portion 523 on the distal side of the first projection 521, and the second projection 522 is connected to the side wall portion 523 on the proximal side of the second projection 522. When an external force is applied to the first projection 521 and the second projection 522, the insides of the slits 524 and 525 bend in the radial direction of the second slider 52 to form movable portions 526 and 527 that allow the first projection 521 and the second projection 522 to move in the radial direction.

A pair of side wall portions 523 are provided at positions facing each other with the central axis interposed therebetween. The side wall portion 523 is disposed in the elongated hole 532 and is disposed to be insertable in the insertion hole 517 of the first slider 51.

Next, an aspect of the ligation device 1 and a connection method will be described.

In the operation unit 5, the first slider 51 and the second slider 52 are externally installed onto the handle 53. The first slider 51 and the second slider 52 are provided to be slidable with respect to the handle 53 in the longitudinal axis L direction. A distal end surface 5202 of the distal wall portion 520 of the second slider 52 is a first contact surface which is able to come into contact with an end surface 5320 of the elongated hole 532 on the distal side.

The proximal end of the operation wire 7 is fixed to the wire fixing portion 5141 of the inner surface 514 of the proximal finger hooking wall portion 511 of the first slider 51. As shown in FIG. 5, the operation wire 7 extends toward the distal side from the wire fixing portion 5141 of the first slider 51 in the longitudinal axis L direction. The operation wire 7 is inserted through the insertion hole 517 of the first slider 51, a space between the side wall portions 523 of the second slider 52, the wire insertion hole 528 of the second slider 52, and the wire insertion hole 535 of the handle 53 and is inserted into the sheath 8. The distal end of the operation wire 7 extends to the distal portion of the sheath 8. Since the sheath 8 is fixed to the handle 53, when the first slider 51 is advanced and retracted with respect to the handle 53, the operation wire 7 moves relative to the sheath 8. As the operation wire 7 advances and retracts the connector 71 protrudes and withdraws from the distal end 81 of the sheath 8. That is, the connector 71 moves with respect to the sheath 8 by the movement of the first slider 51 with respect to the handle 53. Therefore, by adjusting the position of the first slider 51 with respect to the handle 53, it is possible to adjust the position of the connector 71 with respect to the distal end 81 of the sheath 8.

In the present embodiment, when the first slider 51 is advanced in the distal side direction with respect to the handle 53, the operation wire 7 is advanced. As shown in FIG. 1, when the first slider 51 is located at the distal end portion of the handle 53, the distal end of the operation wire 7 and the connector 71 protrude from the distal end 81 of the sheath 8. At a protrusion position where the connector 71 protrudes from the distal end 81 of the sheath 8, the clip unit 3 becomes a state of being fitted to the connector 71.

The first slider 51 and the second slider 52 are configured to be able to be fitted to each other. As shown in FIGS. 5 and 7, the side wall portion 523 of the second slider 52 is inserted into the insertion hole 517 of the first slider 51 and is configured to be able to advance and retract in the insertion hole 517. The pair of side wall portions 523 of the second slider 52 is disposed at positions facing the inner holes 5131 of the first slider 51. The first projection 521 of the second slider 52 is configured to be able to be fitted to the inner hole 5131 and the locking recess 519 of the first slider 51. The second projection 522 of the second slider 52 is configured to be able to be fitted to the inner hole 5131 of the first slider 51.

When the first projection 521 or the second projection 522 is fitted to the inner hole 5131, the first slider 51 and the second slider 52 are fitted to each other. The first projection 521 and the second projection 522 of the side wall portion 523 project outward of the inner wall of the insertion hole 517 in the radial direction. Since the side wall portion 523 is disposed in an opening of the elongated hole 532 of the handle 53, when the first projection 521 or the second projection 522 comes into contact with the inner wall of the insertion hole 517, the movable portions 526 and 527 of the side wall portion 523 are bent inward in the radial direction, and the first slider 51 and the second slider 52 are allowed to move relative to each other in the longitudinal axis L direction. In a fitting state in which the first projection 521 or the second projection 522 is inserted into the inner hole 5131, when the operator pushes the outer projecting portion 543 of the switch member 54 inward in the radial direction (a second operation), the switch member 54 is moved inward in the radial direction in the hollow portion 513. As a result, the inner projecting portion 542 enters the inner hole 5131, and the contact surface 5421 of the inner projecting portion 542 comes into contact with the first projecting portion 521 or the second projection 522. As a result, the first projection 521 or the second projection 522 inserted into the inner hole 5131 is pressed by the switch member 54, and the movable portions 526 and 527 are bent inward in the radial direction, and thus the fitting between the first slider 51 and the second slider 52 is released.

The first slider 51 and the second slider 52 fitted to each other are configured to be able to advance and retract with respect to the handle 53 while the fitting state is held. In the following description, the first slider 51 and the second slider 52 fitted to each other are referred to as a fitting slider.

As shown in FIG. 7, in a state in which the first projection 521 is fitted to the inner hole 5131, the side wall portion 523 of the second slider 52 is exposed from the first slider 51, and the length (the movable distance of the first slider 51) between the proximal end of the first slider 51 and the proximal end of the elongated hole 532 in the longitudinal axis L direction becomes a first length L1 (a limitation state). The distance between the inner hole 5131 and the locking recess 519 in the longitudinal axis L direction is substantially equal to the distance between the first projection 521 and the second projection 522. Therefore, as shown in FIG. 5, when the second projection 522 is fitted to the inner hole 5131, the side wall portion 523 is accommodated in the insertion hole 517, and the first projection 521 is fitted to the locking recess 519. When the second projection 522 is fitted to the inner hole 5131, the length of the fitting slider in the longitudinal axis L direction becomes shorter than that in the limitation state, and the length (the movable distance of the first slider 51) between the proximal end of the first slider 51 and the proximal end of the elongated hole 532 in the longitudinal axis L direction becomes a second length L2 (a limitation release state). The first length L1 is shorter than the second length L2. Therefore, the movement range of the fitting slider in the elongated hole 532 differs between the limitation state in which the length of the fitting slider is long and the limitation release state in which the length of the fitting slider is short. Specifically, in the limitation state, the movement range of the first slider 51 with respect to the handle 53 is shorter than in the limitation release state. When the fitting slider is in the limitation state, the position where the first slider 51 allows to advance in the distal side direction with respect to the handle 53 is restricted as compared with the case of the limitation release state. That is, the second slider 52 functions as a stopper that restricts the advance movement position of the first slider 51.

In the limitation release state, the first slider 51 is allowed to further advance to the distal side than in the limitation state. Since the operation wire 7 is fixed to the first slider 51, when the fitting slider in the limitation release state is advanced to the most distal side as much as possible, the connector 71 becomes a protrusion state in which the connector 71 protrudes from the distal end 81 of the sheath 8. On the other hand, in the limitation state, the position where the first slider 51 is allowed to advance to the most distal side is on a further proximal side than that in the limitation release state. The position where the first slider 51 is allowed to advance to the most distal side in the limitation state is a position where the connector 71 is located on the proximal side from the distal end 81 of the sheath 8 and the connector 71 is accommodated in the sheath 8.

Next, a usage aspect of the ligation device 1 and a connection method will be described.

Figure 11:
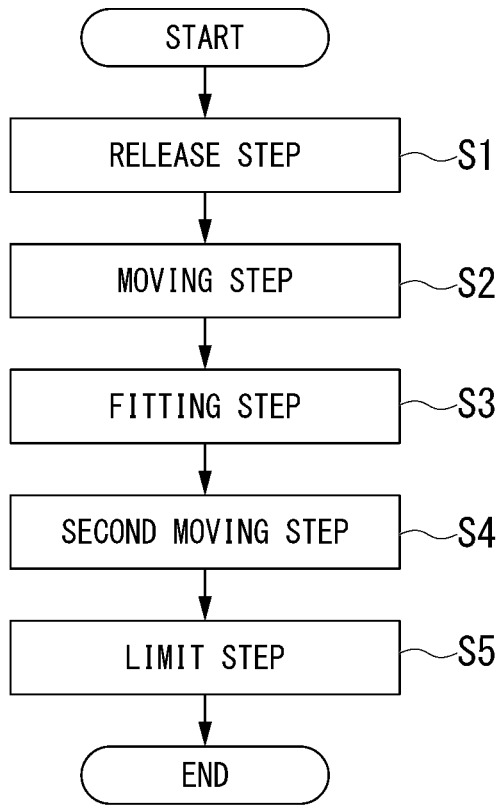
FIG. 11 is a flowchart showing a connection method according to the first embodiment.

FIG. 11 is a flowchart showing a connection method according to the present embodiment.

The connector 71 is protruded from the distal end 81 of the sheath 8 in order to mount the clip unit 3 on the distal end 81 of the sheath 8. Specifically, the operator pushes the outer projecting portion 543 of the switch member 54 in the direction of intersecting the advance and retract movement direction, releases the fitting of the first projection 521 to the inner hole 5131, and then moves the first slider 51 to advance. When the first slider 51 is advanced with respect to the second slider 52 and the second projection 522 faces the inner hole 5131, the second projection 522 is fitted to the inner hole 5131 and the first projection 521 is locked to the locking recess 519, and thus the fitting slider becomes the limitation release state. In this way, unlike a advance operation (a first operation) of the first slider 51 that advances the operation wire 7, with a pushing operation (a second operation) of the outer projecting portion 543 of the switch member 54, the fitting slider is switched to the limitation release state from the limitation state (a release step S1).

In the above description, the state in which the first slider 51 is advanced with respect to the second slider 52 to shorten the length of the fitting slider has been described as the limitation release state, but the limitation release state in the present specification is not limited to this. For example, a state in which the operator pushes the outer projecting portion 543 of the switch member 54 to release the fitting of the first projection 521 to the inner hole 5131 (in other words, a state in which the first slider 51 is allowed to advance with respect to the second slider 52) is also included in the limitation release state. Even in a state in which the operator pushes the outer projecting portion 543 of the switch member 54 to release the fitting of the first projection 521 to the inner hole 5131, the second slider 52 comes into contact with an edge of the elongated hole 532 with the advance operation (the first operation) of the first slider 51, and the first slider 51 is capable of advancing with respect to the second slider 52. Therefore, the movement range of the first slider 51 with respect to the handle 53 in the limitation release state is longer than the movement range of the first slider 51 in the limitation state. That is, in the limitation release state, the movement range of the fitting slider in the elongated hole 532 is longer than the movement range thereof in the limitation state.

Subsequently, the operator advances the fitting slider in the limitation release state with respect to the handle 53 and advances the connector 71 to the protrusion position (a moving step S2). The connector 71 is held in the protrusion position, and the proximal end of the clip unit 3 accommodated in a cartridge (not shown) is brought close to the connector 71. When the proximal locking end 25 of the connecting rod 2 is pressed against the connector 71, the locking projection 26 is pushed against the connector 71, and thus the legs 24 are elastically deformed outward in the radial direction, the separation distance between the locking projections 26 increases, and the tip end 74 of the connector 71 enters between the pair of legs 24. When the connector 71 enters the fitting hole 28, the legs 24 return to its original position and the proximal portion of the connector 71 come into contact with the locking projection 26. As a result, the connector 71 is held by the proximal fitting portion 27, and the clip unit 3 is fitted to the connector 71 (a fitting step S3).

Subsequently, the connector 71 is retracted with an operation of moving the fitting slider to the proximal side of the handle 53, and the connector 71 connected to the connecting rod 2 is accommodated in the sheath 8 (a second moving step S4). As shown in FIG. 6, at an accommodation position where the connector 71 is accommodated in the sheath 8, the proximal fitting portion 27 of the connecting rod 2 is inserted into the sheath 8 and the movement of the pair of legs 24 outward in the radial direction is restricted. As a result, the sheath 8 restricts that the fitting between the connector 71 and the connecting rod 2 is released, and the fitting between the connector 71 and the connecting rod 2 is held.

Subsequently, the operator pushes the outer projecting portion 543 of the switch member 54 to release the fitting between the second projection 522 and the inner hole 5131 and then retracts the first slider 51 with respect to the second slider 52. Since the distal end surface 5192 of the locking recess 519 is inclined, when the first slider 51 retracts from the limitation release state, the movable portion 527 is bent along the inclination of the distal end surface 5192, and the first projection 521 smoothly comes off the locking recess 519. When the first slider 51 retracts and the first projection 521 faces the inner hole 5131, the first projection 521 is fitted to the inner hole 5131, and the fitting slider becomes the limitation state (a limit step S5).

The operator inserts an endoscope (not shown) into the patient's body in advance. The operator inserts the ligation device 1 from the operation unit side of a treatment tool channel of a treatment tool for an endoscope (not shown) and protrudes the ligation device 1 from the distal end of the channel of the endoscope.

When the fitting slider in the limitation state is moved to the proximal side with respect to the handle 53, the proximal end of the holding tube 4 comes into contact with the distal end 81 of the sheath 8, and the clip unit 3 is held in a state of being extended in the longitudinal axis L direction. Subsequently, the operator pushes the operation unit 5 to the distal side, advances the applicator 100 with respect to the treatment tool channel of the treatment tool for an endoscope, and brings the arm member 30 into contact with the treatment target portion. In this state, when the operator retracts the fitting slider in the limitation state to the proximal side, the holding tube 4 does not retract because it is in contact with the sheath 8, and the connecting rod 2 and the arm member 30 retract with respect to the holding tube 4.

When the arm member 30 retracts with respect to the holding tube 4, the connecting portion 33 enters the holding tube 4. The connecting portion 33 is pushed into the insertion passage of the holding tube 4, and the first arm 31 and the second arm 32 are opened away from each other.

Next, the operator operates an endoscope (not shown), adjusts the orientation and posture of the arm member 30, and presses the arm member 30 toward the treatment target portion. By such an operation, the first arm 31 and the second arm 32 of the arm member 30 in the opened form is disposed around the treatment target portion.

After checking that the treatment target portion is located between the first arm 31 and the second arm 32 on an endoscopic image, the operator grips the handle 53 and moves the fitting slider in the limitation release state to the proximal side. With this operation, the first arm 31 and the second arm 32 are pulled by the operation wire 7 and moved to the proximal side. The first arm 31 and the second arm 32 are retracted while coming into contact with the tapered surface 42 at the distal portion of the holding tube 4 and elastically deformed in a direction in which the first arm 31 and the second arm 32 approach each other. As a result, the claw portions 36 of the first arm 31 and the second arm 32 come close to each other, and the first arm 31 and the second arm 32 are capable of gripping the treatment target portion. At this time, when the pair of projecting pieces 34 enters the insertion hole 41 on the proximal side from the step portion 44, the pair of projecting pieces 34 is frictionally fitted to the insertion hole 41 on the proximal side from the step portion 44. As a result, a state in which the treatment target portion is gripped by the arm member 30 is held.

When the operator further retracts the fitting slider in the limitation state, the pair of projecting pieces 34 protrudes to the proximal side from the opening of the proximal portion of the holding tube 4 and comes into contact with the proximal end of the holding tube 4, and the arm member 30 is locked to the holding tube 4. As a result, the movement of the arm member 30 to the distal side with respect to the holding tube 4 is restricted. The arm member 30 is held by the holding tube 4 in a state of sandwiching the treatment target portion.

When the operator further retracts the fitting slider, a step portion 35 provided on each of the arms 31 and 32 is pushed into the inner wall of the insertion passage of the holding tube 4, and the arm member 30 is fitted into the holding tube 4. If the fitting slider is continuously retracted even after the arm member 30 is fitted into the holding tube 4, the hook portion 23 of the connecting rod 2 buckles, and the locking between the connecting portion 33 and the hook portion 23 is released. As a result, the fitting between the arm member 30, the holding tube 4, and the connecting rod 2 is released, the connection between the arm member 30, the holding tube 4, and the sheath 8 is released, and the treatment target portion is ligated.

When the fitting slider is retracted in a state in which the connecting rod 2 is fitted to the connector 71, the connecting rod 2 is accommodated in the sheath 8. In a state in which the connecting rod 2 is accommodated in the sheath 8, the applicator 100 is removed from the channel of the endoscope, and the fitting operation is completed.

After the treatment target portion is ligated with a first clip unit 3, the applicator 100 is removed from the body, and if necessary, a second clip unit 3 is loaded into the applicator 100 again. Specifically, after the applicator 100 is removed from the body, the operation wire 7 is protruded from the distal end 81 of the sheath 8, and the connecting rod 2 connected to the connector 71 of the operation wire 7 is removed. Next, a second cartridge accommodating the second clip unit 3 is prepared. The operation wire 7 is retracted, the cartridge is brought close to the sheath 8 in the same manner as described above, and the connecting rod 2 and the connector 71 are fitted to each other. As a result, the clip unit 3 is loaded into the applicator 100. In this way, when a plurality of portions of tissue is ligated with a plurality of clip units 3, it is possible to continuously load the clip units 3 without replacement of the applicator 100.

According to the present embodiment, the limitation state in which a movement range of the operation wire 7 with respect to the sheath 8 is restricted to a desired range and the limitation release state in which the limitation is released is capable of being switched. As a result, when the fitting slider is in the limitation state, it is possible to operate the sliders while the connector 71 is held in the accommodation position where the connector 71 is accommodated in the sheath 8. On the other hand, when the fitting slider is in the limitation release state, the connector 71 is capable of being extruded to the protrusion position where the connector 71 protrudes from the distal end 81 of the sheath 8. That is, the second slider 52 limits a movement range of the first slider 51 when the second operation is not performed, and configured to release a limitation of the movement range of the first slider 51 with the second operation and to allow the second link 71 to move toward the protrusion position.

According to the present embodiment, the fitting slider is held in the limitation state until the operation of ligating the treatment target portion with the arm member 30 is performed from a state in which the clip unit 3 is held on the distal side of the sheath 8. As a result, since the most advance movement position of the first slider 51 is restricted, the connector 71 does not protrude from the distal end 81 of the sheath 8 even if the operator mistakenly advances the fitting slider in the distal side direction. In other words, since the connecting portion between the connector 71 and the connecting rod 2 is disposed in the sheath, the movement of the pair of legs 24 outward in the radial direction is restricted, and the fitting between the connector 71 and the connecting rod 2 is held. Therefore, the clip unit 3 does not fall out of the distal side of the sheath 8.

At this time, as shown in FIG. 6, the proximal end surface of the holding tube 4 is in contact with the tip surface of the sheath 8. In the present embodiment, due to manufacturing tolerances of parts, errors during operation, or the like, the holding tube 4 and the sheath 8 may not be in close contact with each other, and the distance therebetween may be almost zero. In this case, since the clip unit 3 and the applicator 100 are connected by the fitting between the connector 71 and the connecting rod 2, the clip unit 3 does not unintentionally fall out of the applicator 100. In the present specification, the case where the distance between the holding tube 4 and the sheath 8 is almost zero is also included in "the holding tube 4 is in contact with the sheath 8."

Even in a case where the fitting slider is advanced in the distal side direction to reopen the arm member 30 after the arm member 30 is closed, the clip unit 3 does not falls out of the distal side of the sheath 8.

Specifically, there is provided a slider (the fitting slider) which is constituted by the first slider 51 and the second slider 52 and is capable of changing the length in the longitudinal axis L direction to two lengths. The second slider 52 functions as a stopper that restricts a movement position of the first slider 51 to the distal side. Since the operation wire 7 is connected to the first slider 51, when the advance movement range of the first slider 51 is limited, the advance movement position of the operation wire 7 with respect to the sheath 8 is capable of being limited. As a result, in a case where it is desirable to hold the connecting rod 2 in a storage position, it is possible to prevent the operation wire 7 from protruding from the distal end 81 of the sheath 8 by making the fitting slider be in the limitation state.

According to the ligation device 1 of the present embodiment, the switch member 54 is moved in the direction intersecting the advance and retract movement direction of the first slider 51. The advance and retract movement direction of the first slider 51 for advancing and retracting the operation wire 7 is different from the direction of pushing the switch member 54. As a result, the operator smoothly operate without confusing the movement operation of the first slider 51 with the switching operation of the limitation state.

In the present embodiment, an example in which the second slider 52 as a stopper is disposed on the distal side of the first slider 51 is shown, but the position of the stopper is not limited to this. For example, a configuration in which the stopper is provided at a position where it overlaps the first slider 51 in the longitudinal axis L direction, and the position of the stopper with respect to the handle 53 is advanced to switch the advance movable range of the first slider 51 with respect to the handle 53, may be employed.

Second Embodiment

Figure 12:
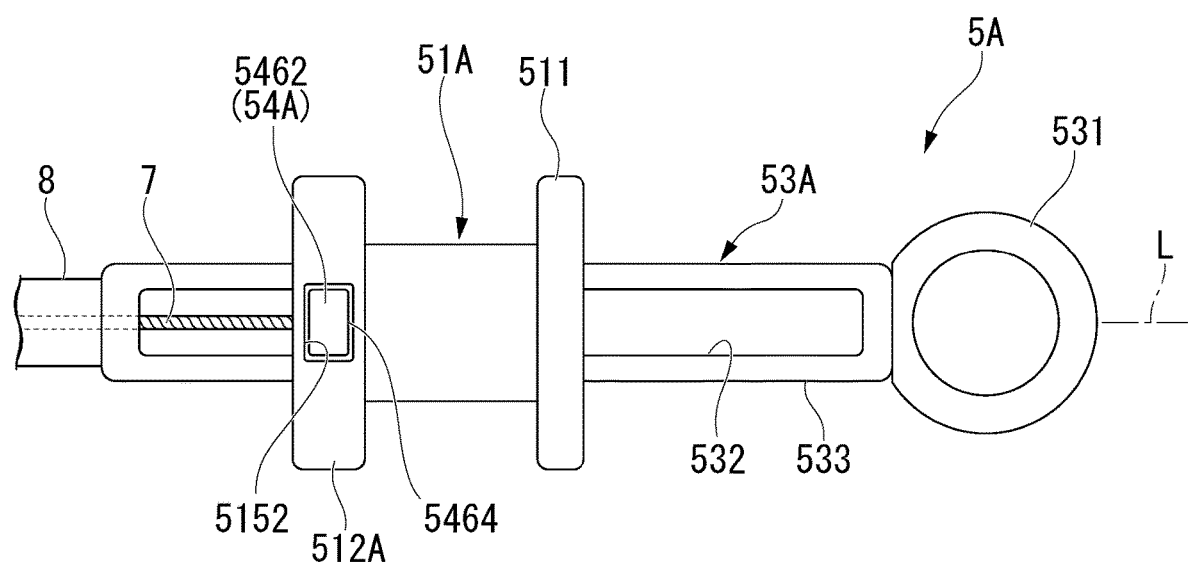
FIG. 12 is a side view showing an operation unit of a ligation device according to a second embodiment.
Figure 13A:
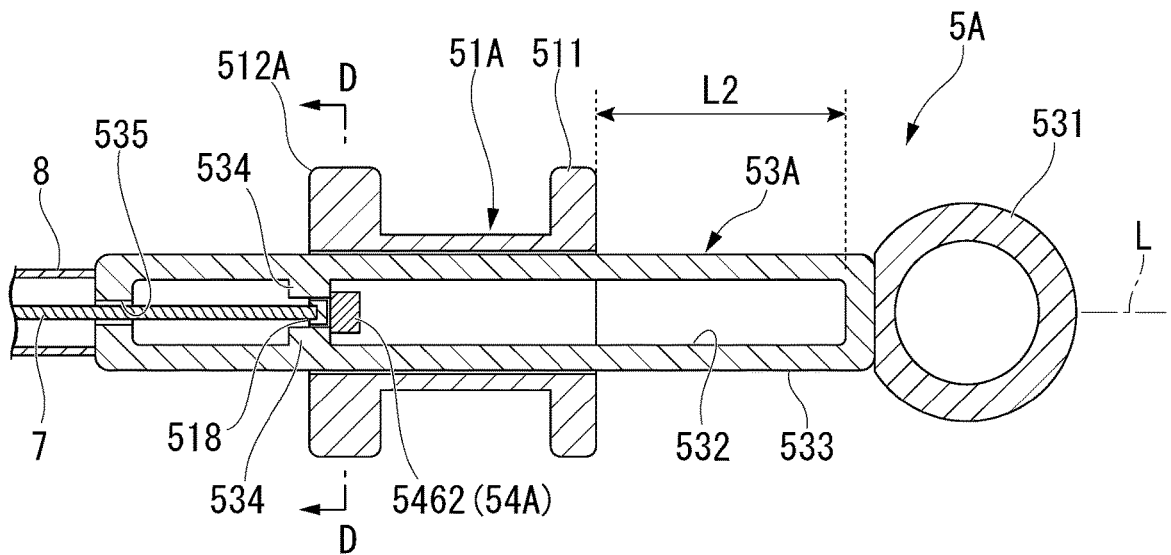
FIG. 13A is a cross-sectional view showing the operation unit of the ligation device according to the second embodiment.
Figure 13B:
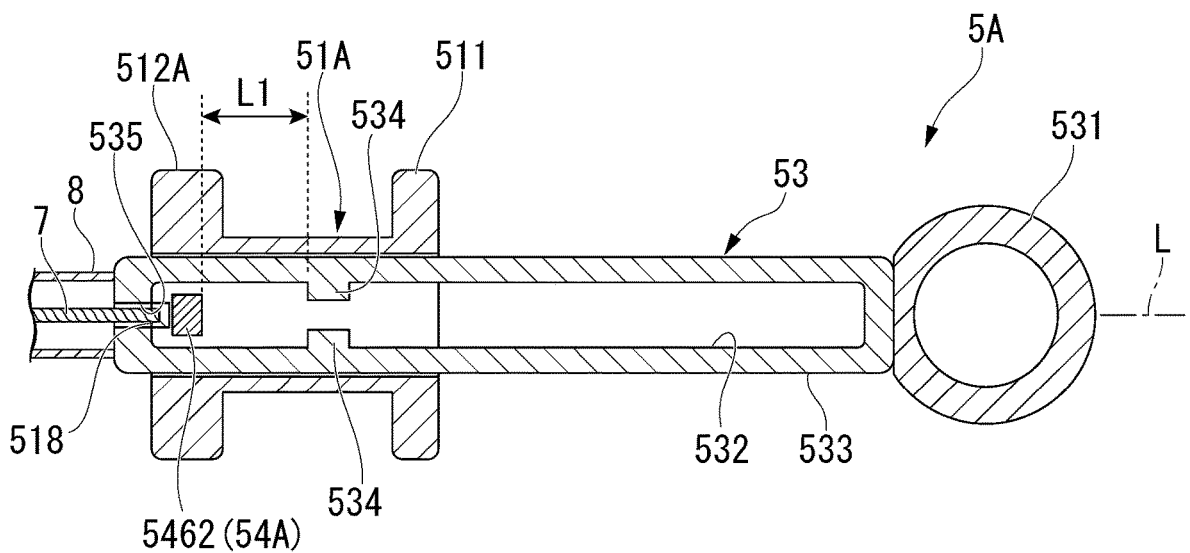
FIG. 13B is a partial cross-sectional view showing the operation unit of the ligation device according to the second embodiment.
Figure 14:
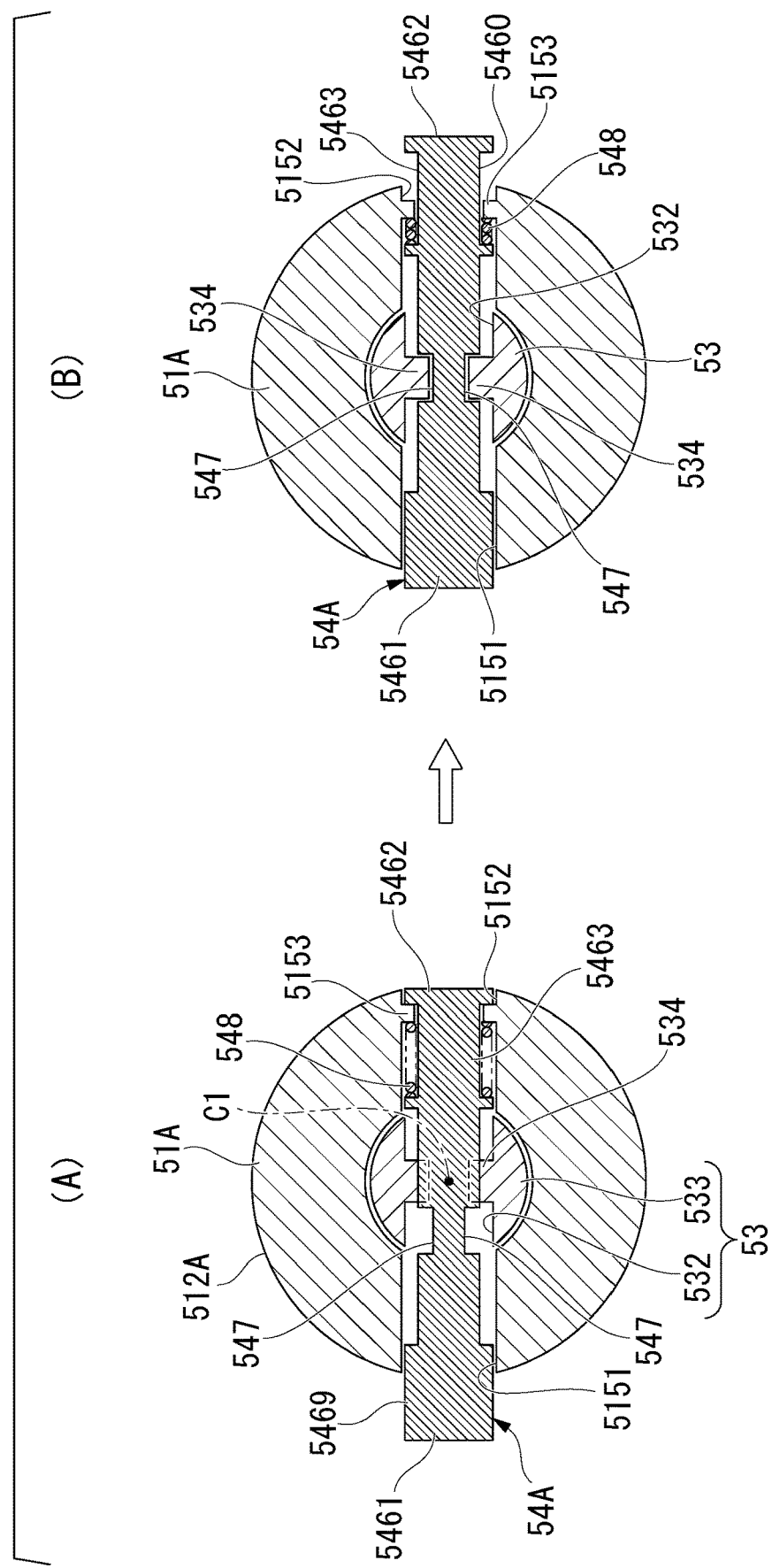
FIG. 14 is a cross-sectional view along line D-D shown in FIG. 13A.

A ligation device 1A according to a second embodiment will be described with reference to FIGS. 12 to 14. In the following description, the same constituent elements as those already described in the first embodiment are designated by the same reference signs, and duplicate description will be omitted. FIG. 12 is a side view showing an operation unit 5A of the ligation device 1A. FIGS. 13A and 13B are cross-sectional views of the operation unit 5A of the ligation device 1A according to the present embodiment in the longitudinal axis L direction. FIG. 14 is a cross-sectional view along line D-D shown in FIG. 13A.

In the ligation device 1A according to the present embodiment, a configuration of the operation unit is different from that of the first embodiment, and a configuration for switching between the limitation release state and the limitation state of a first slider 51 is different from that of the first embodiment. The operation unit 5A of the present embodiment does not include the second slider 52 of the first embodiment.

The operation unit 5A of the present embodiment is provided with a pair of stoppers 534 in the elongated hole 532 of the handle 53. The pair of stoppers 534 projects from the inner wall of the elongated hole 532 in a direction orthogonal to the longitudinal axis L and is formed to face each other. The facing surfaces of the pair of stoppers 534 are separated from each other. As a result, the opening of the elongated hole 532 becomes narrow at the position of the stopper 534.

A configuration of a first slider 51A of the present embodiment is different from that of the first slider 51 of the first embodiment. In the first slider 51A of the present embodiment, configurations of a locking hole and a switch member of the first slider 51A are different from those of the first embodiment. As shown in FIG. 14, a first locking hole 5151 and a second locking hole 5152 communicating with each other inside and outside the first slider 51 are formed in a direction orthogonal to the longitudinal axis L (a diameter direction of the first slider 51). A switch member 54A is inserted into the first locking hole 5151 and the second locking hole 5152.

The switch member 54A is a rod-shaped member longer than the diameter of a distal finger hooking wall portion 512A of the first slider 51A. Both ends of the rod-shaped switch member 54A in an axial direction function as a first switch portion 5461 and a second switch portion 5462. A pair of recesses 547 is formed in the central portion of the switch member 54A in the axial direction. The pair of recesses 547 is substantially rectangular recesses that are open in opposite directions.

In the second switch portion 5462, a groove portion 5463 having a smaller outer peripheral dimension than that of the first switch portion 5461 is formed. The second locking hole 5152 is provided with a rib 5153 projecting from the inner wall of the second locking hole 5152. The groove portion 5463 of the second switch portion 5462 is disposed in the second locking hole 5152. A spring 548 is disposed in the groove portion 5463, and one end of the spring 548 is in contact with the rib 5153. With this configuration, in a natural state, the switch member 54A is biased by the spring 548, and the first switch portion 5461 is held in a state of protruding outward from the first locking hole 5151. When the first switch portion 5461 is pushed toward the insertion hole 517 side of the first slider 51A, the spring 548 is compressed, and the switch member 54 moves from the first locking hole 5151 side toward the second locking hole 5152 side.

As shown in FIGS. 13A and 13B, the pair of stoppers 534 is provided at one location in the elongated hole 532. The pair of recesses 547 is formed to be able to pass through the stoppers 534. In the natural state of the switch member 54A, as shown in (A) of FIG. 14, the first switch portion 5461 protrudes from the first locking hole 5151, and the pair of recesses 547 is deviated outward from the central axis C of the first slider 51A. Therefore, in the natural state, the switch member 54A comes into contact with the stoppers 534, and the movement of the first slider 51A in the longitudinal axis L direction is restricted. On the other hand, when the first switch portion 5461 is pushed toward the central axis C side, the pair of recesses 547 is positioned to face the stoppers 534. As a result, when the first switch portion 5461 is pushed, the switch member 54A is movable while passing through a space between the stoppers 534.

The switch member 54A is slidably inserted into the first locking hole 5151 and the second locking hole 5152 of the first slider 51A. In a limitation state or a limitation release state, a proximal end surface 5464 (see FIG. 12) of the second switch portion 5462 of the switch member 54A comes into contact with the second locking hole 5152 of the first slider 51A. That is, the proximal end surface 5464 of the second switch portion 5462 becomes a first contact surface which is able to come into contact with the handle 53A. The proximal end surface 5464 of the second switch portion 5462 becomes a second contact surface which comes into contact with the first slider 51A.

As shown in FIG. 13A, the operation wire 7 is fixed to a wire fixing portion 518 of the first slider 51A. The switch member 54A is provided on the proximal side from the wire fixing portion 518 in the longitudinal axis L direction of the first slider 51.

That is, the switch member 54A is capable of being switched between the limitation state and the limitation release state with the operation of moving in a direction different from the longitudinal axis L direction which is the moving direction of the first slider 51. As a result, the second slider 52A is capable of being releasing the limitation of the movement range of the first slider 51A with a second operation different from a first operation of moving the first slider 51A. Specifically, as shown in FIG. 13A, when the switch member 54A is located on the proximal side from the stopper 534, it is in the limitation state, and as shown in FIG. 13B, when the switch member 54A is located on the distal side from the stopper 534, it is in the limitation release state.

When the first switch portion 5461 is pushed in a state in which the switch member 54A is in contact with the stopper 534, the switch member 54A passes through a space between the stoppers 534, and the function of restricting the movement range of the switch member 54A by the stopper 534 is released.

According to the ligation device 1A of the present embodiment, as in the first embodiment, the limitation state in which a movement range of the operation wire 7 with respect to the sheath 8 is restricted to a desired range and the limitation release state in which the restriction is released is capable of being switched. As a result, when the fitting slider is in the limitation state, it is possible to operate the fitting slider while the connector 71 is held in the accommodation position where the connector 71 is accommodated in the sheath 8. On the other hand, when the fitting slider is in the limitation release state, the connector 71 is extruded to the protrusion position where the connector 71 protrudes from the distal end 81 of the sheath 8.

According to the ligation device 1A of the present embodiment, the movement direction (the advance and retract movement direction) of the first slider 51A for advancing and retracting the operation wire 7 is different from the direction of pushing the switch member 54A. As a result, the operator smoothly operate without confusing the movement operation of the first slider 51A with the switching operation of the limitation state. When the operator pushes the switch member 54A, the operator can push the switch member 54A by a finger gripping the first slider 51A, for example, a thumb. Accordingly, since the operator operates the switch member 54A while holding the slider by one hand, the operator easily switch the switch member 54A and move the slider.

According to the present embodiment, the fitting slider is held in the limitation state until the operation of ligating the treatment target portion with the arm member 30 is performed from a state in which the clip unit 3 is held on the distal side of the sheath 8. As a result, since the most advance movement position of the first slider 51A is restricted, the connector 71 does not protrude from the distal end 81 of the sheath 8 even if the operator mistakenly advances the fitting slider in the distal side direction. Therefore, the clip unit 3 does not fall out of the distal side of the sheath 8.

In the present embodiment, an example in which the pair of stoppers 534 is provided at one location in the elongated hole 532 is shown, but the number of stoppers is not limited to this. The pair of stoppers may be provided at two or more locations in the elongated hole 532 with separated from each other in the longitudinal axis L direction, for example. In this case, the movable range of the first slider 51 is capable of being adjusted in multiple stages.

Third Embodiment

Figure 15:
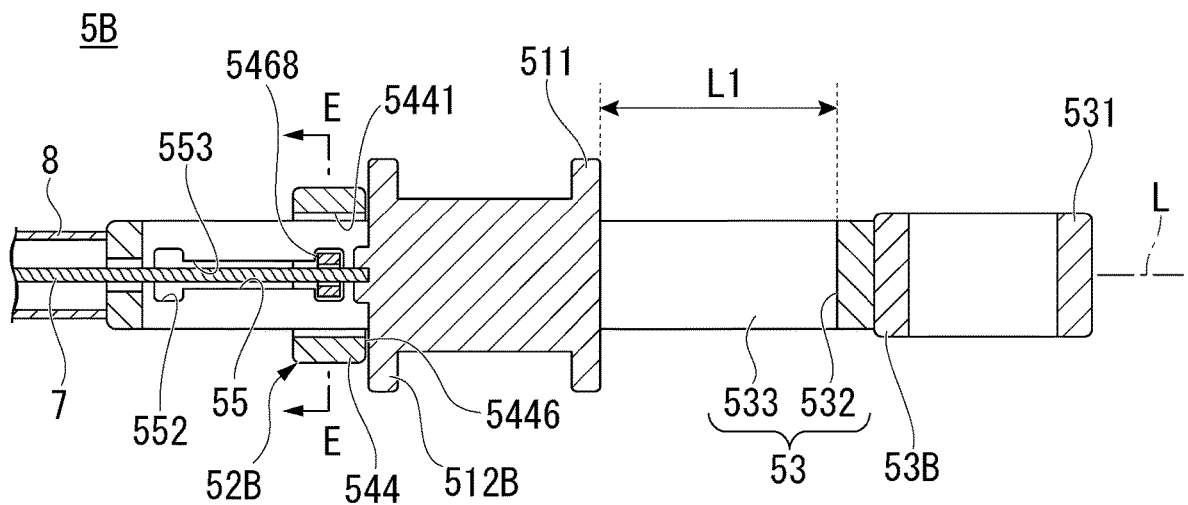
FIG. 15 is a partial cross-sectional view showing an operation unit of a ligation device according to a third embodiment.
Figure 16:
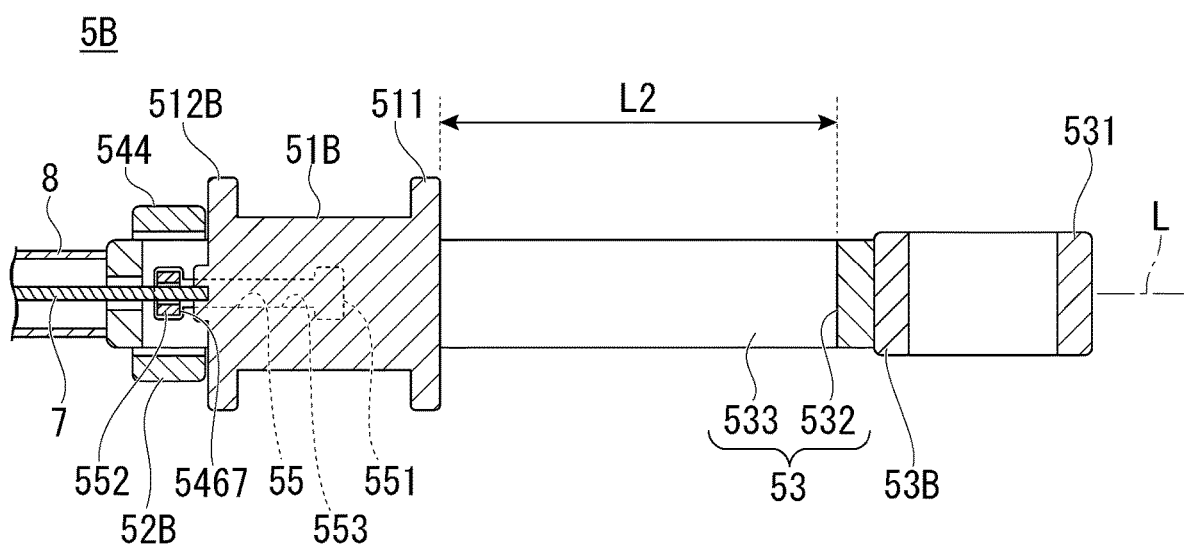
FIG. 16 is a partial cross-sectional view showing the operation unit of the ligation device according to the third embodiment.
Figure 17:
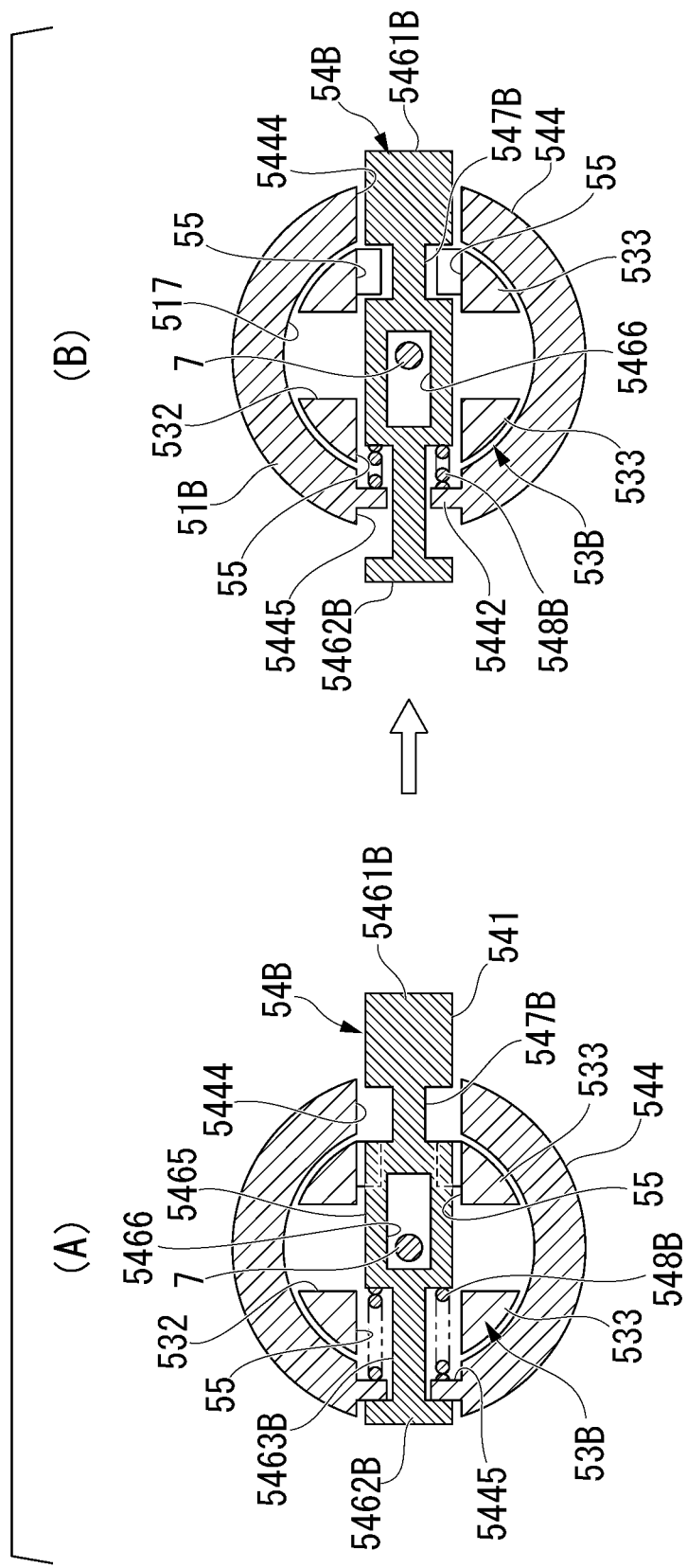
FIG. 17 is a cross-sectional view along line E-E shown in FIG. 15.

A ligation device 1B according to a third embodiment will be described with reference to FIGS. 15 to 17. FIGS. 15 and 16 are cross-sectional views of an operation unit 5B of the ligation device 1B according to the present embodiment in the longitudinal axis L direction. FIG. 17 is a cross-sectional view along line E-E shown in FIG. 15. In the ligation device 1B according to the present embodiment, a configuration of the operation unit is different from that of the first embodiment, and a configuration for switching between the limitation release state and the limitation state of a first slider 51B is different from that of the first embodiment.

As shown in FIGS. 15 and 16, a guide hole 55 extending in the longitudinal axis L direction is formed in the distal portion of the handle 53B. The guide hole 55 is formed to pass through the elongated hole 532 and to penetrate the outer surface of the handle 53B. The guide hole 55 is formed by a proximal opening 551, a distal opening 552, and an intermediate opening 553 being communicated with each other. The distal opening 552 and the proximal opening 551 are located at both ends of the guide hole 55 in the longitudinal axis L direction. The intermediate opening 553 constitutes a space between the proximal opening 551 and the distal opening 552. The proximal opening 551 and the distal opening 552 have a larger opening dimension than that of the intermediate opening 553.

As shown in FIG. 17, two guide holes 55 are provided at positions facing each other with the elongated hole 532 of the handle 53 interposed therebetween. In the cross section orthogonal to the longitudinal axis L direction, a pair of guide holes 55 is formed to extend in a direction intersecting the elongated holes 532.

The operation unit 5B of the present embodiment includes a limiter member 52B instead of the second slider 52 of the first embodiment. The limiter member 52B is a member that restricts the most advance movement position of the first slider 51B. The limiter member 52B is provided on the distal side from the first slider 51B and is externally inserted onto the handle 53B. The operation wire 7 is fixed to the first slider 51B.

The limiter member 52B has a support cylinder 544 having an annular shape, a switch main body 54B, and a spring 548B.

As shown in FIG. 15, the support cylinder 544 is provided with a handle insertion hole 5441 penetrating in the longitudinal axis L direction and is externally inserted onto the handle 53B by the handle 53B being inserted into the handle insertion hole 5441. As shown in FIG. 17, in the support cylinder 544, a first locking hole 5444 and a second locking hole 5445 communicating with each other inside and outside the first slider 51B are formed in a direction orthogonal to the longitudinal axis L (a radial direction of the support cylinder 544). The second locking hole 5445 is provided with a rib 5442 projecting from the inner wall of the second locking hole 5445. A switch main body 54B is inserted into the first locking hole 5444 and the second locking hole 5445.

The switch main body 54B is a rod-shaped member longer than the diameter of the support cylinder 544. Both ends of the rod-shaped switch main body 54B in an axial direction function as a first switch portion 5461B and a second switch portion 5462B. An intermediate body 5465 having a rectangular cross section is provided between the first switch portion 5461B and the second switch portion 5462B of the switch main body 54B. A wire insertion passage 5466 through which the operation wire 7 is inserted is formed inside the intermediate body 5465. A first recess 547B is formed between the first switch portion 5461B and the intermediate body 5465, and a second recess 5463B is formed between the second switch portion 5462B and the intermediate body 5465. The first recess 547B and the second recess 5463B are a pair of substantially rectangular recesses that is open in opposite directions, respectively. As shown in FIG. 17, the dimension of the second recess 5463B in the axial direction of the switch main body 54B is longer than the dimension of the first recess 547B. The intermediate body 5465 has a dimension that allows it to enter the distal opening 552 and the proximal opening 551.

The second recess 5463B is disposed in the second locking hole 5445. A spring 548 is disposed in the second recess 5463B, and one end of the spring 548 is in contact with the rib 5442. With this configuration, as shown in (A) of FIG. 17, in a natural state, the switch main body 54B is biased by the spring 548, and the first switch portion 5461B is held in a state of protruding outward from the first locking hole 5444. As shown in (B) of FIG. 17, when the first switch portion 5461B is pushed toward the insertion hole 517 side of the first slider 51B, the spring 548 is compressed, and the switch main body 54B moves from the first locking hole 5444 side toward the second locking hole 5445 side.

The switch main body 54B moves along the guide hole 55 when the first switch portion 5461B is pressed and the first recess 547B faces the intermediate opening 553 of the guide hole 55. On the other hand, in the switch main body 54B, in the natural state, the first recess is disposed outside the intermediate opening 553, the first recess 547B and the intermediate opening 553 do not face each other, and the intermediate body 5465 and the guide hole 55 come in contact with each other. That is, a distal end surface 5468 or a proximal end surface 5467 of the intermediate body 5465 is a first contact surface that comes into contact with the handle 53B. As a result, the switch main body 54B becomes immovable along the guide hole 55 in the natural state. When the switch main body 54B is caused to be in a natural state at the proximal opening 551 or the distal opening 552, the position of the switch main body 54B is restricted to the proximal end or the distal end of the guide hole 55. When the switch member 54A is located at the distal opening 552, it becomes the limitation release state, and when the switch member 54A is located at the proximal opening 551, it becomes the limitation state.

In the limiter member 52B in the limitation release state or the limitation state, a position in the longitudinal axis L direction with respect to the handle 53B is held. The first slider 51B moves in the longitudinal axis L direction with respect to the handle 53B and comes into contact with a proximal surface 5446 of the support cylinder 544 of the limiter member 52B. The proximal surface 5446 of the limiter member 52B is a second contact surface which is able to come into contact with the first slider 51B.

According to the ligation device 1B of the present embodiment, it is possible to switch between the limitation release state and the limitation state by the relative movement of the switch main body 54B with respect to the handle 53B. According to the ligation device 1B of the present embodiment, since the limiter member 52B is provided, it is possible to switch between the limitation release state and the limitation state with a simple operation. When the clip unit 3 is mounted on the sheath 8, the holding tube 4 does not easily come off the sheath 8.

According to the ligation device 1B of the present embodiment, the movement direction of the first slider 51B for advancing and retracting the operation wire 7 is different from the direction of pushing the switch main body 54B. As a result, the operator smoothly operate without confusing the movement operation of the first slider 51B with the switching operation of the limitation state.

Fourth Embodiment

Figure 18:
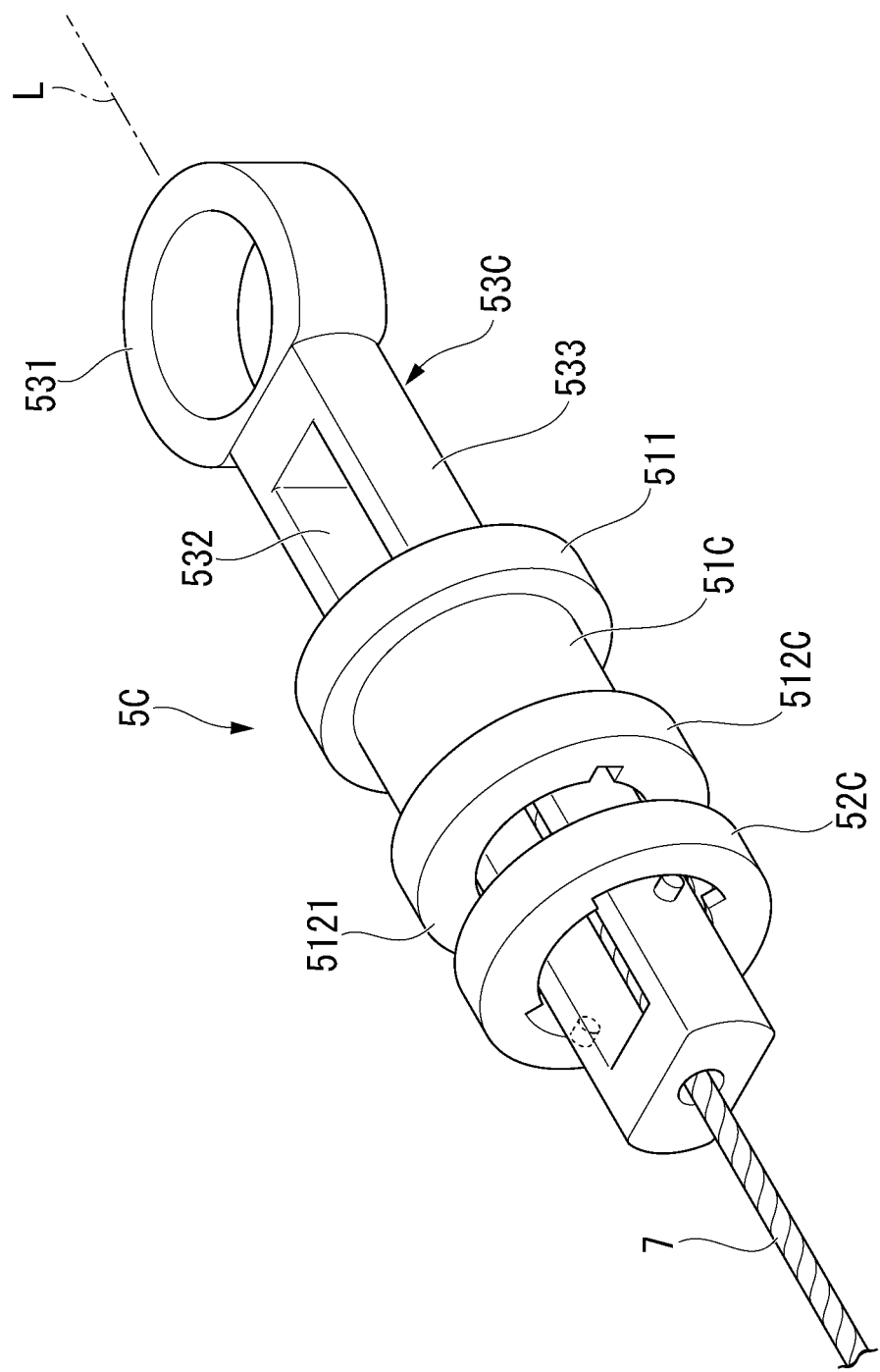
FIG. 18 is a perspective view showing an operation unit of a ligation device according to a fourth embodiment.
Figure 19:
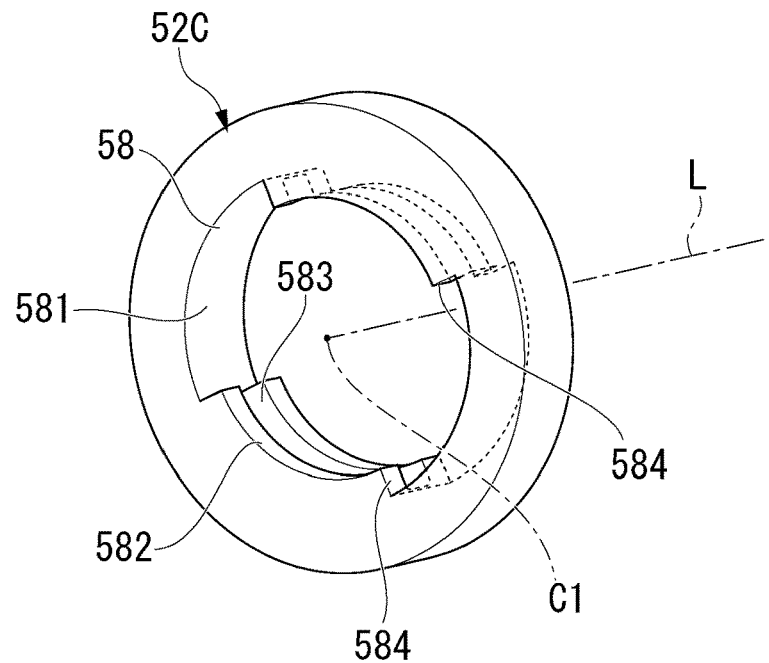
FIG. 19 is a perspective view showing a second slider of the fourth embodiment.
Figure 20:
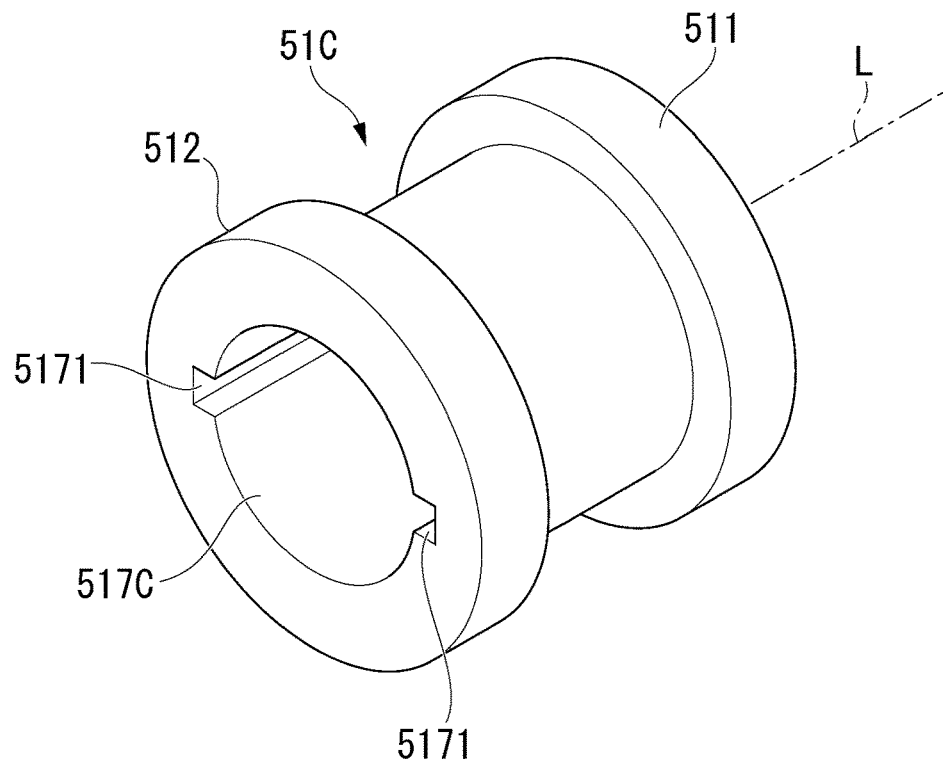
FIG. 20 is a perspective view showing a first slider of the fourth embodiment.
Figure 21:
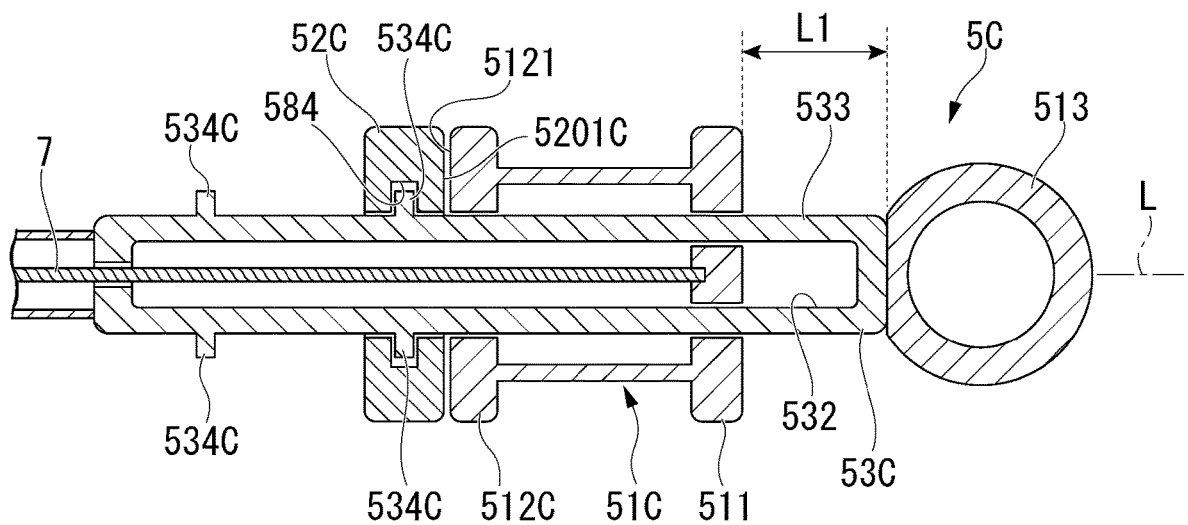
FIG. 21 is a cross-sectional view showing the operation unit of the ligation device according to the fourth embodiment.
Figure 22:
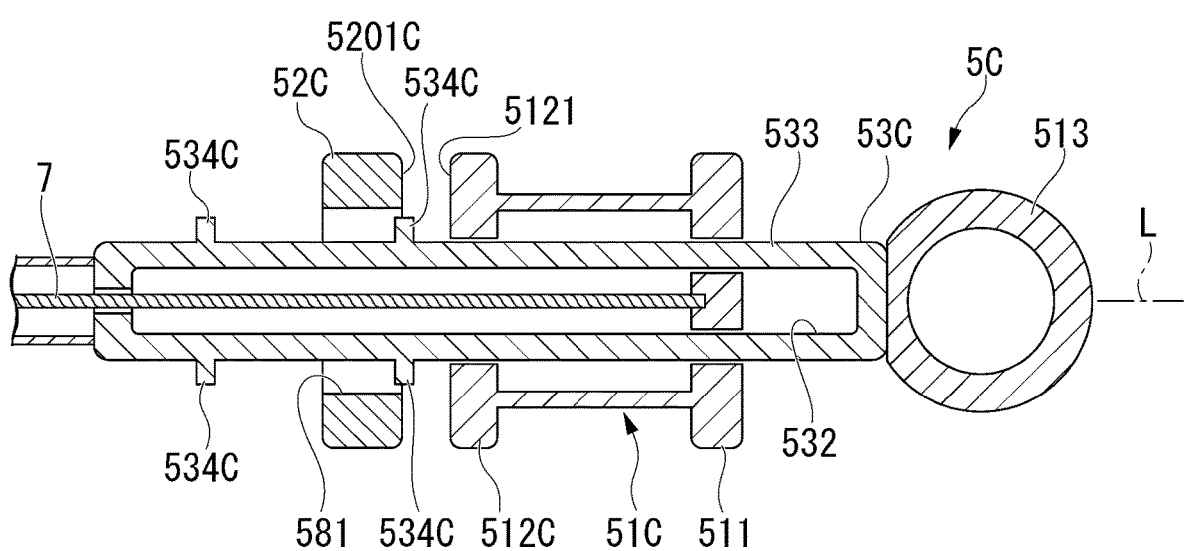
FIG. 22 is a cross-sectional view showing the operation unit of the ligation device according to the fourth embodiment.
Figure 23:
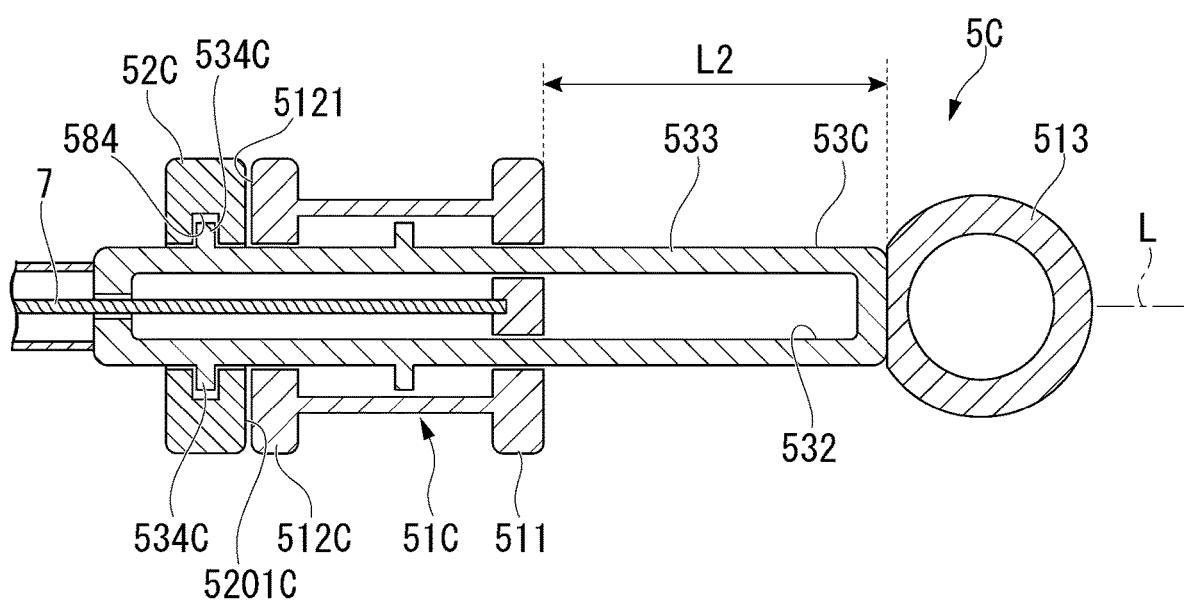
FIG. 23 is a cross-sectional view showing the operation unit of the ligation device according to the fourth embodiment.

A ligation device 1C according to a fourth embodiment will be described with reference to FIGS. 18 to 23. FIG. 18 is a perspective view showing an operation unit 5C of the ligation device 1C according to the present embodiment. FIG. 19 is a perspective view showing a second slider 52C of the present embodiment. FIG. 20 is a perspective view showing a first slider 51C of the present embodiment. FIGS. 21 to 23 are cross-sectional views showing the operation unit 5C of the ligation device 1C.

In the ligation device 1C according to the present embodiment, a configuration of the handle is different from that of the first embodiment, and a configuration for switching between the limitation release state and the limitation state of a first slider 51C is different from that of the first embodiment.

As shown in FIG. 19, the second slider 52C (a switch member) is a ring-shaped member, and the central axis C is disposed along the longitudinal axis L. A handle insertion hole 58 is formed in the second slider 52C along the longitudinal axis L direction. The handle insertion hole 58 has a large diameter portion 581 and a small diameter portion 582. A step portion 584 is formed at a boundary between the large diameter portion 581 and the small diameter portion 582.

In the small diameter portion 582, an annular groove 583 (a first contact surface) that is recessed outward from the inner peripheral surface in the radial direction is formed. The annular groove 583 communicates with the large diameter portion 581 at the step portion 584.

In the handle 53C, a pair of outer stoppers 534C projecting outward on the outer surface of a side wall portion 533 is formed. The pair of outer stoppers 534C is projections having a circle columnar shape which project in a direction orthogonal to the longitudinal axis L. As shown in FIGS. 21 to 23, the pair of outer stoppers 534C is provided at two locations while being separated from each other in the longitudinal axis L direction.

The projecting length of each outer stopper 534C from the outer surface of the side wall portion 533 has a length that allows it to enter the annular groove 583 of the small diameter portion 582 and not to come into contact with the inner circumferential surface of the large diameter portion 581 in a state of being extrapolated to the second slider 52C. Therefore, when the outer stopper 534C is located in the large diameter portion 581, the second slider 52C is capable of moving in the longitudinal axis L direction with respect to the handle 53C. When the outer stopper 534C is located in the small diameter portion 582, the second slider 52C is immovably locked in the longitudinal axis L direction.

As shown in FIG. 20, in the first slider 51C, a slide groove 5171 extending in the longitudinal axis L direction is formed in the inner circumferential surface of an insertion hole 517C. The slide groove 5171 is formed from the distal end to the proximal end of the first slider 51A. Two slide grooves 5171 are formed to face the inner circumferential surface of the insertion hole 517C. The outer stopper 534C is located in the slide groove 5171 (a first position), and the first slider 51C is configured to be slidable in the longitudinal axis L direction with respect to the handle 53C.

By being rotated around the central axis Cl (rotated around the advance and retract movement direction), the second slider 52C switches between a state in which the movement in the longitudinal axis L direction with respect to the handle 53C is restricted and a state in which the restriction on the movement in the longitudinal axis L direction is released. Specifically, when the position of the small diameter portion 582 around the central axis Cl of the second slider 52C overlaps the position of the outer stopper 534C, the outer stopper 534C enters the annular groove 583 to come into contact with the annular groove 583. The inner surface of the annular groove 583 is a first contact surface that comes into contact with the handle 53C. The distal end surface 5121 of the first slider 51C comes into contact with the proximal end surface 5201C (a second contact surface) of the second slider 52C. When the movement of the second slider 52C in the longitudinal axis L direction is restricted, the first slider 51C is capable of advancing to a position where it comes into contact with the proximal end surface 5201C of the second slider 52C.

As shown in FIG. 23, when the second slider 52C is locked to the outer stopper 534C located on the distal side, the first slider 51C becomes the limitation release state. As shown in FIG. 21, when the second slider 52C is locked to the outer stopper 534C located on the proximal side, the first slider 51C becomes the limitation state. When the second slider 52C is moved between the outer stopper 534C located on the distal side and the outer stopper 534C located on the proximal side, the second slider 52C is rotated to be disposed, as shown in FIG. 22, in the large diameter portion 581 (a second position) at which the stopper 534C does not come into contact with the second slider 52C and is moved in the longitudinal axis L direction.

According to the ligation device 1C of the present embodiment, it is possible to switch between the limitation release state and the limitation state by the rotation of the second slider 52C with respect to the handle 53C. According to the ligation device 1C of the present embodiment, since the second slider 52C is provided, it is possible to switch between a releasing mode and a fitting mode with a simple operation. When the clip unit 3 is mounted on the sheath 8, the holding tube 4 does not easily come off the sheath 8.

In the above, the embodiments have been described in detail with reference to the drawings, but the specific configuration is not limited to the embodiments, and design changes and the like within a range not departing from the gist of the present invention are also included.

In addition, the constituent elements shown in the above-described embodiments and modification examples can be appropriately combined and configured.

What is claimed is:
1. A ligation device comprising:
a clip unit including a first link; and
an applicator, that includes:
a sheath;
an operation wire inserted into the sheath and configured to operate the clip unit,
a second link provided on the operation wire and being configured to move between a protrusion position and an accommodation position,
the protrusion position being when the second link is connected to the first link and the second link protrudes from the sheath,
the accommodation position being when the second link is restricted from releasing the first link and the second link is accommodated in the sheath;
a slider connected to the operation wire and configured to move in a first direction with a first operation; and
a limiter including a switch member configured to move in a second direction that intersects the first direction with a second operation,
wherein the limiter is configured to limit movement of the slider when the second operation is not performed, and configured to release the limited movement of the slider with the second operation and to allow the second link to move toward the protrusion position.

2. The ligation device according to claim 1, wherein, when the first link and the second link are fitted to each other and the slider is advanced maximally in a state where the movement range of the slider is limited by the limiter, a connection portion between the first link and the second link is located in the sheath.

3. The ligation device according to claim 1, wherein:
the clip unit includes a holding tube having a cylindrical shape, the holding tube configured to accommodate an arm member that includes a first arm and a second arm, and
the first link is positioned to protrude from the holding tube on a proximal of the clip unit.

4. The ligation device according to claim 3, wherein, when the first link and the second link are fitted to each other and the slider is advanced maximally in a state where the movement range of the slider is limited by the limiter, the holding tube and the sheath come into contact with each other.

5. The ligation device according to claim 1,
wherein the slider is configured to move the second link by advancing and retracting.

6. The ligation device according to claim 5,
wherein the applicator includes a handle to which the slider is attached to be able to advance and retract,
wherein the limiter includes:
a first contact surface configured to contact with the handle; and
a second contact surface configured to contact with the slider, and
wherein at least one of the first contact surface or the second contact surface is provided on the switch member and move together with the switch member in the intersecting direction.

7. The ligation device according to claim 1,
wherein the slider is configured to move the second link by advancing and retracting,
wherein the switch member is configured to rotate around an advance and retract direction of the slider, and
wherein the limiter is configured to release the limited movement of the slider by the switch member being rotated with the second operation.

8. The ligation device according to claim 7,
wherein the applicator includes a handle attached to the slider to allow an operator to advance and retract the slider;
wherein the limiter includes:
a first contact surface that can contact the handle, and
a second contact surface that can contact with the slider, and
wherein at least one of the first contact surface and the second contact surface is provided on the switch member and that can rotate with the switch member.

9. An applicator comprising:
a sheath;
an operation wire inserted into the sheath and configured to connect with a clip unit;
a link connected to the operation wire and configured to connect to the clip unit at a protrusion position where the link protrudes from the sheath, the link being configured to be prevent release of the clip unit at an accommodation position where the link is accommodated in the sheath;
a slider connected to the operation wire and is configured to move in a first direction with a first operation; and
a limiter including a switch member configured to move in a second direction that intersects the first direction with a second operation,
wherein the limiter is configured to:
limit movement of the slider and maintain the link in the accommodation position when the second operation is not performed, and
release the limited movement of the slider with the second operation and allow the link to move toward the protrusion position.

10. The applicator according to claim 9,
wherein the slider is configured to move the link by advancing and retracting.

11. The applicator according to claim 10, wherein:
the applicator includes a handle attached to the slider, the handle being configured to allow an operator to advance and retract the slider;
the limiter includes:
a first contact surface configured to contact the handle; and
a second contact surface configured to contact the slider, and
at least one of the first contact surface or the second contact surface is provided on the switch member to move together with the switch member in the intersecting direction.

12. The applicator according to claim 9,
wherein the slider is configured to move the operation wire by advancing and retracting,
wherein the switch member is configured to rotate around an advance and retract direction of the slider, and
wherein the limiter is configured to release the limited movement of the slider by rotation of the switch member with the second operation.

13. The applicator according to claim 9,
wherein the slider is configured to move the link by advancing and retracting,
wherein the switch member is configured to rotate around an advance and retract direction of the slider, and
wherein the limiter is configured to release the limited movement of the slider by rotating the switch member with the second operation.

14. A connection method of a clip unit in a ligation device comprising:
a clip unit that has a first link;
a second link provided at a distal end of an operation wire inserted into a sheath;
a slider connected to the operation wire; and
a limiter configured to limit movement of the slider, the connecting method comprising:
restricting movement of the slider with the limiter with a first operation, the restricted movement of the slider being in a first direction;
releasing the restricted movement of the slider by the limiter with a second operation by operating a switch in a second direction that intersects the first direction;
first moving the second link with the first operation from an accommodation position where the second link is accommodated in the sheath to a protrusion position where the second link protrudes from the sheath;
fitting the second link to the first link at the protrusion position;
then moving the second link that is fitted to the first link with the first operation to the accommodation position; and again restricting the movement of the slider with the second operation.

\* \* \* \* \*